US008753819B2

(12) United States Patent
Perlin et al.

(10) Patent No.: US 8,753,819 B2
(45) Date of Patent: Jun. 17, 2014

(54) ASSAYS FOR RESISTANCE TO ECHINOCANDIN-CLASS DRUGS

(75) Inventors: David S. Perlin, Chappaqua, NY (US); Steven Park, Whitestone, NY (US); Cameron M. Douglas, Piscataway, NJ (US); Jennifer Nielsen Kahn, East Brunswick, NJ (US); Stephen A. Parent, Belle Mead, NJ (US); Rosemarie Kelly, Westfield, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 1272 days.

(21) Appl. No.: 11/995,966

(22) PCT Filed: Jul. 26, 2006

(86) PCT No.: PCT/US2006/029290
§ 371 (c)(1),
(2), (4) Date: Sep. 21, 2009

(87) PCT Pub. No.: WO2007/014305
PCT Pub. Date: Feb. 1, 2007

(65) Prior Publication Data
US 2010/0075302 A1 Mar. 25, 2010

Related U.S. Application Data

(60) Provisional application No. 60/702,756, filed on Jul. 26, 2005.

(51) Int. Cl.
*C12Q 1/68* (2006.01)
*C12P 19/34* (2006.01)
*C07H 21/04* (2006.01)

(52) U.S. Cl.
USPC .................. 435/6.12; 435/91.2; 53/24.3

(58) Field of Classification Search
None
See application file for complete search history.

(56) References Cited

U.S. PATENT DOCUMENTS

| 4,965,188 A | 10/1990 | Mullis et al. |
| 5,487,972 A | 1/1996 | Gelfand et al. |
| 5,538,848 A | 7/1996 | Livak et al. |
| 5,821,353 A * | 10/1998 | Douglas et al. ............ 536/23.74 |
| 5,925,517 A | 7/1999 | Tyagi et al. |

FOREIGN PATENT DOCUMENTS

| EP | 0931834 A2 | 7/1999 |
| WO | 03054233 A1 | 7/2003 |

OTHER PUBLICATIONS

Ohyama et al. FKS1 mutations responsible for selective resistance of *Saccharomyces cerevisiae* to the novel 1,3-beta-glucan synthase inhibitor arborocandin C. Antimicrobial Agents and chemotherapy, vol. 48, No. 1, pp. 319-322, 2004.*
Kondoh, O. et al. Differential sensitivity between FKs1p and FKs2p against a novel 1, 3-beta-glucan synthase inhibitor, Aerothricin 1. J. Biol. Chem., vol. 277, No. 44, pp. 41744-41749, 2002.*
Kellner, EM. et al. Coccidioides posadassi contains a single 1,3-beta-glucan synthase gene that appears to be essential for growth. Eukaryotic Cell, vol. 4, No. 1, pp. 111-120, Jan. 2005.*
Ohyamaet al., "FKS1 Mutations Responsible for Selective Resistance of *Saccharomyces cerevisiae* to the Novel 1,3-b-Glucan Synthase Inhibitor Arborcandin C,"Antimicrobial Agents and Chemotherapy (2004): vol. 48, No. 1, pp. 319-322.
Eng et al., "The yeast FKS1 gene encodes a novel membrane protein, mutations in which confer FK506 and cyclosporin A hypersensitivity and calcineurin-dependent growth," Gene (1994): vol. 151, pp. 61-71.
Thompson et al., "A Gluan Synthase FKS1 Homolog in *Ryptococcus neoformans* Is single Copy and Encodes an Essential Function,"; Journal of Bacteriology (Jan. 1999): vol. 181, No. 2, pp. 444-453.
Douglas et al., "Identification of the FKS1 Gene of *Candida albicans* as the Essential Target of 1,3-b-D-Glucan Synthase Inhibitors,"; Antimicrobial Agents and Chemotherapy (Nov. 1997): vol. 41, No. 11, pp. 2471-2479.
Favre et al., "Multiple amino acid substitutions in lanosterol 14a-demethylase contribute to azole resistance in *Candida albicans*," Microbiology (Oct. 1999): 145(10):2715-2725.
Mann et al., "Mutations in *Aspergillus fumigatus* resulting in reduced susceptibility to posaconazole appear to be restricted to a single amino acide in cytochrome P450 14alpha-demethylase," Antimicrobial Agents and Chemotherapy (Feb. 2003): 47(2):577-581.
Stevens et al., Studies of the paradoxical effect of caspofungin high drug concentrations, Diagnostic Microbiology and Infectioius Diseases (Mar. 1, 2005) 51(3):173-178.
Balashov et al., "Assessing resistance to the echinocandin antifungal drug caspofungin in *Candida albians* by proflign mutatiosn in FKS1," Antimicrobial Agents and Chemotherapy (2006) 50(6):2058-2063.
Park et al., "Specific substitutions in the echinocandin target Kks1p account for reduced susceptibility of rare laboratory and clinical *Candida* sp. 1solates," Antimicrobial Agents and Chemotherapy (2005) 49(8):3264-3273.
Afonina et al., "Minor groove binder-conjugated DNA probes for quantitative DNA detection by hybridization-triggered fluorescence," BioTechniques (2002) 32(4):940-949.
Li et al., "A new class of homogeneous nucleic acid probes based on specific displacement hybridization," Nucleic Acids REsearch (2002) 30(2):1-9.
Whitcombe et al., "Detection of PCR products usign self-probing amplicons and fluorescence," Nature Biotechnology (Aug. 17, 1999) 17:804-807.

* cited by examiner

*Primary Examiner* — Prabha Chunduru
(74) *Attorney, Agent, or Firm* — Fox Rothschild LLP; Gerard P. Norton; Jianming Hao

(57) ABSTRACT

Nucleic acid amplification assays for mutations to two short sections of the fungal gene FKS1. Mutations in these target sequences have been shown to correlate with resistance to echinocandin-class drugs. Assays may include detection by sequencing or by labeled hybridization probes. Also, primers, probes and reagent kits for performing such assays.

12 Claims, 10 Drawing Sheets

FIGURE 1A

SEQ. ID NO. 1

GAATTCTAAAATTAGCAAAAAAAAATTGTGTGTGCGTGTGAGTTGGTAAAAGAAACGAAAAAAAAGCAATT
TTTACATTTGCTATCTTCAGTTTTAAGGCATTTGATTACCCAATTTGAAATAAGTCCAAAAGATATCCATT
TAAAACAAACAGTATTTCCTGTATTTATCAATTTATCAAAGAATCTAGCATTCATATATAATCAATCTAAC
TTCTTGGTGTTTAAGAAATCCTCCTACTACTCACAAATCTCGAGCAAAATTTTTTTTTTGTTTGATCTCAT
ACGATTTCAGGTACAATTTTTTTAAAAGGAAAAAGTTTGCAATATCTTACATAATTTGGATTGCTGTTTTT
ATTATAGGGTCAGATTCACATTTCCAGATCTCAATAGAAACCCAGTTTCCCATTAATTTAAGAGATATCAG
TTTATTTCGATTACAAATTGAGTTGTCACAACTACGTTTCACATATACTATTATTTCAATTTCCCATCATT
GCAACAACAAACGAAAAATTAATTCTTGATTTTGCTGTTTTTTTTTGTGAACAAAAAGCACACAAACATAC
ACACAATACATTTAATAACAACAATTTTCAAAATAATAATAACTTTTCCTTTTTCTTTTAATTTCCCCCCT
TCTTTTTTTTTAAATATTAAAAACCAACACCCAACTGATATACTAACTTATCTTTTTTTTCAAATTAGATG
TCGTATAACGATAATAATAATCATTATTACGACCCTAATCAACAGGGCGGTATGCCACCTCATCAAGGAGG
AGAAGGGTATTACCAACAACAGTATGATGATATGGGTCAACAACCACACCAACAAGATTATTACGATCCAA
ATGCTCAATATCAACAACAACCATATGACATGGATGGATATCAAGACCAAGCCAACTATGGTGGTCAACCA
ATGAATGCCCAGGGTTATAATGCTGACCCAGAAGCCTTTCTGACTTTAGTTATGGTGGTCAAACTCCTGG
AACTCCTGGTTATGATCAATACGGTACTCAATACACCCCATCTCAAATGAGTTATGGTGGTGATCCAAGAT
CTTCTGGTGCTTCAACACCAATTTATGGTGGTCAAGGTCAAGGTTACGATCCAACTCAATTCAATATGTCA
TCGAACTTGCCATATCCAGCTTGGTCTGCTGATCCTCAAGCTCCAATTAAGATTGAACACATCGAAGATAT
TTTCATTGATTTGACTAATAAATTTGGTTTCCAAAGAGATTCTATGAGAAACATGTTTGATTACTTTATGA
CATTGTTGGACTCGAGATCTTCCCGTATGTCACCAGCTCAGGCCTTGTTGAGTTTACATGCTGATTATATT
GGTGGTGACAATGCCAATTATAGAAAATGGTATTTTTCTTCACAACAAGATTTGGATGATTCCTTAGGTTT
TGCTAATATGACTTTAGGTAAAATTGGTAGAAAAGCCAGAAAAGCTTCCAAGAAATCCAAAAAAGCTAGAA
AAGCTGCTGAAGAACATGGTCAAGATGTCGATGCTCTTGCTAATGAATTAGAAGGTGATTATTCATTGGAA
GCCGCTGAAATCAGATGGAAAGCCAAGATGAACTCTTTGACTCCAGAAGAAAGAGTAAGAGACCTTGCTCT
TTATTGTTGATATGGGGTGAAGCCAATCAAGTTCGTTTTACTCCTGAATGTTTGTGTTACATTTACAAAT
CTGCCACTGATTATTTAAATTCTCCATTGTGTCAACAAAGACAAGAACCAGTGCCTGAAGGTGATTACTTG
AACCGTGTGATCACTCCACTTTACAGATTCATCAGATCTCAAGTTTATGAAATTTATGATGGAAGATTTGT
CAAGCGTGAAAAAGACCACAACAAGGTCATTGGTTATGATGATGTCAATCAATTGTTTTGGTACCCAGAAG
GTATTTCCAGAATTATTTTTGAAGATGGAACCAGATTGGTTGATATCCCTCAAGAAGAAACGTTTCTTGAAA
TTAGGTGAAGTTGAATGGAAGAATGTTTTCTTCAAAACTTATAAGGAAATCAGAACCTGGTTGCATTTCGT
TACCAATTTTAATAGAATCTGGATTATCCATGGTACCATCTACTGGATGTACACTGCTTACAACTCCCCAA
CCTTGTATACTAAACATTATGTCCAAACCATAAATCAACAACCACTTGCTTCGTCAAGATGGGCTGCTTGT
GCCATTGGTGGTGTTCTTGCTTCATTTATTCAAATTCTTGCCACACTTTTCGAATGGATTTTCGTGCCTAG
AGAATGGGCCGGTGCTCAACATTTGAGTCGTCGTATGCTATTTTTGGTGTTAATTTTCTTACTCAATTTGG
TTCCACCAGTTTATACATTCCAAATTACCAAATTGGTGATTTATTCGAAATCGGCATATGCTGTGTCGATT
GTTGGATTTTTCATTGCTGTGGCCACTTTAGTATTCTTTGCCGTCATGCCATTGGGTGGTTTATTCACTTC
ATACATGAACAAGAGATCAAGAAGATATATTGCATCACAAACATTTACTGCCAACTACATTAAATTGAAAG
GTTTAGATATGTGGATGTCTTATTTGTTATGGTTTTTGGTTTTCCTTGCCAAATTGGTTGAATCTTATTTC
TTCTCGACTTTGTCTTTAAGAGATCCTATTAGAAACTTGTCGACCATGACAATGAGATGTGTTGGTGAAGT
TTGGTACAAAGATATTGTTTGTAGAAACCAAGCCAAGATTGTCTTGGGGTTGATGTATCTTGTTGATTTGT
TATTGTTCTTTTTGGATACTTATATGTGGTACATTATTTGTAACTGTATCTTCTCCATTGGTCGTTCATTC
TATTTGGGTATTTCCATTTTGACTCCTTGGAGAAACATTTTCACCAGATTGCCAAAGAGAATTTATTCCAA
GATTTTAGCTACCACGGAAATGGAAATCAAATATAAACCTAAAGTTTTGATTTCACAAATTTGGAATGCCA
TTGTTATTTCCATGTACAGAGAACATTTGTTAGCCATTGATCACGTTCAAAAATTATTGTATCATCAAGTT
CCATCTGAAATTGAAGGCAAGAGAACTTTGAGAGCTCCAACTTTCTTTGTTCTCAAGATGACAACAATTT
TGAAACGGAATTTTTCCCAAGAAATTCTGAAGCTGAAAGAAGAATTTCATTTTTCGCTCAATCTTTGGCTA
CACCAATGCCAGAACCATTACCAGTTGATAATATGCCAACTTTTACTGTTTTCACTCCTCATTATTCGGAA
AAGATTTTGTTATCTTTGAGAGAAATCATTAGAGAAGATGATCAATTCTCAAGAGTGACATTATTGGAATA
TTTGAAACAATTACATCCAGTTGAATGGGATTGTTTTGTTAAGGACACCAAGATTTGGCTGAAGAAACTG
CTGCTTATGAAAATGGTGATGATTCTGAAAAATTATCTGAAGATGGATTGAAATCCAAGATTGATGATTTA
CCATTCTATTGTATTGGTTTCAAGTCTGCCGCCCCTGAATATACTTTAAGAACAAGAATTTGGGCTTCATT
GAGATCCCAAACTTTGTACAGAACTGTATCTGGGTTTATGAATTATGCCAGAGCCATTAAATTGTTATACA
GAGTGGAAAACCCAGAATTGGTTCAATATTTCGGTGGTGACCCTGAAGGATTAGAATTAGCTTTAGAAAGA
ATGGCCAGAAGAAAGTTTAGATTTTTGGTTTCTATGCAAAGATTGTCTAAATTCAAAGATGATGAAATGGA

FIGURE 1B

SEQ. ID NO. I (cont...)

```
AAATGCTGAGTTCTTATTGCGTGCTTACCCTGATTTGCAAATTGCTTACTTGGATGAAGAACCGGCTTTGA
ATGAGGACGAGGAACCAAGAGTATACTCTGCCTTGATTGATGGTCATTGTGAAATGTTAGAAAATGGTAGA
CGTCGTCCTAAATTCAGAGTTCAATTGTCTGGTAATCCAATTTTGGGTGATGGTAAATCTGATAATCAAAA
TCATGCGGTTATTTTCCATAGAGGTGAATATATTCAATTGATTGATGCTAATCAAGATAATTATTTGGAAG
AATGTTTGAAGATTAGATCAGTTTTGGCTGAATTTGAAGAAATGAATGTTGAACATGTTAATCCATATGCA
CCAAATTTGAAATCTGAAGATAATAACACCAAGAAGGATCCAGTGGCATTTTTGGGTGCTAGAGAATATAT
TTTCTCAGAAAATTCTGGTGTTTTGGGTGATGTTGCTGCTGGTAAAGAACAAACTTTTGGTACATTGTTTG
CAAGAACTTTGGCACAAATTGGAGGTAAATTGCATTATGGTCATCCGGATTTTTTGAATGCTACATTTATG
TTAACTAGAGGTGGTGTTTCTAAAGCACAAAAGGGTTTACATTTGAATGAAGATATTTATGCTGGTATGAA
TGCCATGATGAGAGGTGGTAAAATCAAGCATTGTGAATATTATCAATGTGGTAAAGGTAGAGATTTAGGTT
TTGGATCCATTTTGAATTTCACCACCAAGATTGGTGCTGGTATGGGAGAACAAATGCTTTCAAGAGAATAT
TTCTATTTGGGTACTCAACTTCCATTGGATAGATTTTTGTCATTTTACTATGGTCATCCAGGTTTCCATAT
TAATAACTTGTTTATTCAATTGTCTTTACAAGTGTTTATTTTGGTGTTGGGTAACTTGAATTCATTAGCTC
ATGAAGCTATCATGTGTTCTTACAACAAAGATGTCCCAGTTACTGATGTTTTGTATCCATTTGGTTGTTAC
AATATTGCTCCTGCCGTTGATTGGATTAGACGTTATACTTTGTCTATTTTCATTGTTTTCTTCATTTCTTT
CATTCCATTGGTTGTACAAGAATTGATTGAAAGAGGGGTATGGAAAGCGTTCAAAGATTTGTTAGACATT
TTATTTCCATGTCACCATTTTTCGAAGTTTTCGTTGCCCAAATTTATTCATCATCGGTTTTCACTGATTTG
ACCGTTGGTGGTGCTAGATATATTTCCACTGGTAGAGGTTTTGCCACTTCAAGAATTCCATTTTCAATCTT
GTATTCACGTTTTGCTGATTCATCCATTTATATGGGAGCAAGATTGATGTTGATTTTATTATTTGGTACAG
TTTCTCATTGGCAAGCACCATTATTATGGTTCTGGGCTTCATTATCGGCTTTAATGTTCTCCCCATTCATT
TTCAATCCTCATCAATTTGCTTGGGAAGACTTTTTCCTTGATTACAGAGATTTCATTAGATGGTTATCTAG
AGGTAACACTAAATGGCACAGAAACTCATGGATTGGTTATGTTAGACTTTCTAGATCACGTATCACTGGTT
TCAAACGTAAGTTGACTGGTGATGTTTCTGAAAAAGCTGCTGGTGATGCTTCAAGAGCTCATAGATCCAAT
GTTTTGTTTGCTGATTTCTTACCAACATTGATTTATACTGCTGGTCTTTATGTTGCTTATACTTTTATTAA
TGCTCAAACTGGGGTTACTAGTTATCCATATGAAATCAATGGATCTACTGATCCACAACCAGTTAATTCTA
CTTTGAGACTTATTATTTGTGCTTTAGCTCCAGTTGTTATTGATATGGGATGTTTAGGTGTTTGTCTTGCC
ATGGCATGTTGTGCTGGTCCAATGTTAGGATTATGTTGTAAAAAGACTGGTGCTGTTATTGCTGGTGTTGC
CCATGGTGTTGCCGTCATTGTTCATATTATTTTCTTTATTGTTATGTGGGTCACTGAAGGTTTCAATTTTG
CCAGATTAATGTTGGGTATTGCCACCATGATTTATGTTCAAAGATTATTATTCAAGTTTTGACATTATGT
TTCTTGACTAGAGAATTTAAGAATGATAAAGCCAATACTGCTTTCTGGACTGGTAAATGGTATAATACTGG
TATGGGATGGATGGCTTTTACTCAACCATCTCGTGAATTTGTTGCTAAAATCATTGAAATGTCGGAATTTG
CTGGTGATTTCGTTTTGGCACATATTATATTATTCTGTCAATTACCATTATTGTTTATTCCATTAGTTGAT
AGATGGCATTCAATGATGTTATTCTGGTTGAAACCATCAAGATTGATTAGACCACCAATTTATTCTTTGAA
ACAAGCCAGATTAAGAAAGAGAATGGTGAGAAAATATTGTGTTTTATATTTTGCCGTGTTGATATTATTTA
TTGTCATTATTGTTGCACCAGCAGTTGCTTCGGGACAAATTGCTGTTGATCAATTTGCCAATATTGGTGGA
TCTGGTTCTATTGCTGATGGATTATTCCAACCAAGAAATGTCAGTAATAATGATACTGGTAATCATAGACC
AAAAACCTACACTTGGAGTTATTTGAGTACTCGTTTTACTGGAAGTACCACCCCTTATTCTACAAATCCAT
TCAGAGTTTAAGAGTTTAAGAGATTAAGCGGGGGCGGAAGTGGTTTATTCATTTATAATTATTTCATTTA
TTCATAAATGGT
```

FIGURE 2

SEQ. ID NO. 2

```
MSYNDNNNHYYDPNQQGGMPPHQGGEGYYQQQYDDMGQQPHQQDYYDPNAQYQQQPYDMDGYQDQANYGGQ
PMNAQGYNADPEAFSDPSYGGQTPGTPGYDQYGTQYTPSQMSYGGDPRSSGASTPIYGGQGQGYDPTQFNM
SSNLPYPAWSADPQAPIKIEHIEDIFIDLTNKFGPQRDSNRNMPDYFMTLLDSRSSRMSPAQALLSLHADY
IGGDNANYRKWYFSSQQDLDDSLGFANMTLGKIGRKARKASKKSKKARKAAEEHGQDVDALANELEGDYSL
EAAEIRWKAKMNSLTPEERVRDLALYLLIWGEANQVRFTPECLCYIYKSATDYLNSPLCQQRQEPVPEGDY
LNRVITPLYRPIRSQVYEIYDGRPVKREKDHNKVIGYDDVNQLFWYPEGISRIIPEDGTRLVDIPQEERPL
KLGEVEWKNVFFKTYKEIRTWLHFVTNFNRIWIIHGTIYWMYTAYNSPTLYTKHYVQTINQQPLASSRWAA
CAIGGVLASFIQILATLPEWIFVPREWAGAQHLSRRMLFLVLIFLLNLVPPVYTFQITKLVIYSKSAYAVS
IVGFFIAVATLVPFAVMPLGGLFTSYMNKRSRRYIASQTPTANYIKLKGLDMWMSYLLWFLVFLAKLVESY
FFSTLSLRDPIRNLSTMIMRCVGEVWYKDIVCRNQAKIVLGLHYLVDLLLFFLDTYMWYIICNCIPSIGRS
FYLGISILTPWRNIPTRLPKRIYSKILATTEMEIKYKPKVLISQIWNAIVISMYREHLLAIDHVQKLLYHQ
VPSEIEGKRTLRAPTFFVSQDDNNFETEFFPRNSEAERRISFPAQSLATPMPEPLPVDNMPTPTVPTPHYS
EKILLSLREIIREDDQFSRVTLLEYLKQLRPVEWDCFVKDTKILAEETAAYENGDDSEKLSEDGLKSKIDD
LPFYCIGFKSAAPEYTLRTRIWASLRSQTLYRTVSGFMNYARAIKLLYRVENPELVQYFGGDPEGLELALE
RMARRKFRPLVSMQRLSKPKDDEMENAEFLLRAYPDLQIAYLDEEPALNEDEEPRVYSALIDGHCEMLENG
RRRPKFRVQLSGNPILGDGKSDNQNHAVIFHRGEYIQLIDANQDNYLEECLKIRSVLAEFEEMNVEHVNPY
APNLKSEDNNTKKDPVAPLGAREYIFSENSGVLGDVAAGKEQTFGTLFARTLAQIGGKLHYGHPDFLNATF
MLTRGGVSKAQKGLHLNEDIYAGNNAMMRGGKIKHCEYYQCGKGRDLGFGSILNFTTKIGAGMGEQMLSRE
YFYLGTQLPLDRFLSFYYGHPGFHINNLFIQLSLQVFILVLGNLNSLAHEAIMCSYNKDVPVTDVLYPPGC
YNIAPAVDWIRRYTLSIFIVFPISPIPLVVQELIERGVWKAFQRFVRHFISMSPFFEVFVAQIYSSSVFTD
LTVGGARYISTGRGPATSRIPFSILYSRFADSSIYMGARLMLILLFGTVSHWQAPLLWFWASLSALMFSPF
IFNPHQFAWEDFFLDYRDFIRWLSRQHTKWHRNSWIGYVRLSRSRITGFKRKLTGDVSEKAAGDASRAHRS
NVLFADFLPTLIYTAGLYVAYTFINAQTGVTSYPYEINGSTDPQPVNSTLRLIICALAPVVIDMGCLGVCL
AMACCAGPMLGLCCKKTGAVIAGVAHGVAVIVHIIFFIVMWVTEGFNFARLMLGIATMIYVQRLLPKFLTL
CFLTREFKNDKANTAFWTGKWYNTGMGWMAFTQPSREFVAKIIEMSEFAGDFVLAHIILFCQLPLLFIPLV
DRWHSMMLFWLKFSRLIRPPIYSLKQARLRKRMVRKYCVLYFAVLILFIVIIVAPAVASGQIAVDQFANIG
GSGSIADGLFQFRNVSNNDTGNHRPKTYTWSYLSTRFTGSTTFYSTNPFRV
```

FIGURE 3

SEQ ID NO. 3

ScFks1p:  Phe$_{639}$   Leu   Val   Leu   Ser   Leu   Arg   Aps$_{646}$

SEQ ID NO. 4

CaFKS1p:  Phe$_{641}$   Leu   Thr   Leu   Ser   Leu   Arg   Asp$_{648}$

FIGURE 4

| SEQ ID NO. | Oligonucleotide | Sequence* | 5' Modification | 3' Modification | Purpose |
|---|---|---|---|---|---|
| 5 | CAFKS1-F1719 | CATTGCTGTGGCCACTTTAG | None | None | Sequencing primer |
| 6 | CAFKS1-R2212 | GATTTCCATTTCCGTGGTAGC | None | None | Sequencing primer |
| 7 | HS1SN2 | GCCAAATTGGTTGAATCTTA | None | None | Real-time PCR primer |
| 8 | HS1AN2 | GTCATGGTCGACAAGTTTCT | None | None | Real-time PCR primer |
| 9 | T-WT | AAAAATCTCTTAAAGACAAAGTCAAGAAAAA | None | None | Wild type target |
| 10 | T-T1933C | AAAAATCTCTTAAAGGCAAAGTCAAGAAAAA | None | None | T1933C Mutation target |
| 11 | T-C1934A | AAAAATCTCTTAAATACAAAGTCAAGAAGAAAA | None | None | C1934A Mutation target |
| 12 | T-C1934T | AAAAATCTCTTAAAAACAAAGTCAAGAAGAAAA | None | None | C1934T Mutation target |
| 13 | T-T1929A | AAAAATCTCTTAAAGACAATGTCAAGAAAAA | None | None | T1929A SNP Target |
| 14 | T-T1929A-T1933C | AAAAATCTCTTAAAGGCAATGTCAAGAAAAA | None | None | T1929A and T1933C Mutations target |
| 15 | T-T1929A-C1934A | AAAAATCTCTTAAATACAATGTCAAGAAGAAAA | None | None | T1929A and C1934A Mutations target |
| 16 | T-T1929A-C1934T | AAAAATCTCTTAAAAACAATGTCAAGAAGAAAA | None | None | T1929A and C1934T Mutations target |
| 17 | HS1-WT | CGCGAGTTCTTGACWTTGTCTTTAAGAGATCTCGCG | FAM | Dabcyl | Wild type probe |
| 18 | HS1-T1933C | CGCGAGTCTTGACWTTGCCTTTAAGAGATCTCGCG | HEX | Dabcyl | T1933C Mutation probe |
| 19 | HS1-C1934A | CGCGAGCTTCTTGACWTTGTATTTAAGAGATCTCGCG | HEX | Dabcyl | C1934A Mutation probe |
| 20 | HS1-C1934T | CGCGAGCTTCTTGACWTTGTTTTTAAGAGATCTCGCG | HEX | Dabcyl | C1934T Mutation probe |

AMPLIFICATION PLOTS

AMPLIFICATION PLOTS

AMPLIFICATION PLOTS

AMPLIFICATION PLOTS

AMPLIFICATION PLOTS

ASSAYS FOR RESISTANCE TO ECHINOCANDIN-CLASS DRUGS

CROSS-REFERENCE TO RELATED APPLICATIONS

This Application is a National Stage Application based on International Application No. PCT/US2006/029290, filed Jul. 26, 2006, which claims priority benefit of U.S. Provisional Application No. 60/702,756, filed Jul. 26, 2005, the disclosures of which are incorporated herein by reference.

TECHNICAL FIELD

This invention relates to nucleic acid assays for fungi.

BACKGROUND

Fungal infections are a significant cause of morbidity and mortality in severely ill patients, and their impact is exacerbated by a failure to rapidly diagnose and effectively treat these infections. The widespread use of antifungal agents has resulted in selection of naturally resistant fungal species, as well as the emergence of resistance in susceptible species. Treatment of fungal disease is hampered by the availability of few classes of antifungal drugs. Recently, caspofungin was introduced clinically as the first of a new class of echinocandin drugs that target the fungal cell wall by blocking $\beta\text{-}(1 \rightarrow 3)$-D-glucan synthase. Caspofungin use is growing rapidly, and clinical isolates of *Candida* species with reduced in vitro susceptibility are being reported with a strong correlation between treatment failure and high in vitro values of minimum inhibitory concentration, or MIC. As patient exposure to caspofungin increases, and as the other echinocandin drugs, including micafungin and anidulafungin, enter the market, it is anticipated that the number of clinical isolates with elevated MIC values will rise.

An aspect of this invention is nucleic-acid assays that detect genetic mutations associated with resistance to echinocandin-drugs in fungi, including but not limited to fungi of the genus *Candida*.

Another aspect of this invention is such nucleic-acid assays that employ exponential nucleic acid amplification of specified regions encoding the FKS1 protein, coupled preferably either with sequencing or detection utilizing labeled allele-discriminating probes.

Another aspect of this invention is kits of reagents and oligonucleotide sets of primers and probes for performing the foregoing assays.

SUMMARY

Echinocandins are the first new major antifungal drug class to enter the market in decades. Maintenance of the fungal cell wall integrity is essential, as a fungus cannot survive without this structure, or even if it is markedly altered in some way. The wall is an extracellular matrix with a layered organization consisting of an outer layer of glycoproteins and an inner layer of carbohydrate polymers including glucan, chitin and galactomannan. In saprophytic and pathogenic fungi, the carbohydrate layer is comprised mainly of $\beta(1 \rightarrow 3)$-glucan and $\alpha(1 \rightarrow 3)$-glucan, but it also contains some $\beta(1 \rightarrow 6)$-glucan and chitin. Glucans are also released from the fungal cell wall as exopolymers into the blood of patients with fungal infections, and are known to activate a wide range of innate immune responses. The fungal cell wall is a dynamic structure, as constitutive polymers are constantly being chemically modified and rearranged during cell wall biosynthesis. For example, Fks1p, the presumptive catalytic subunit of the glucan synthase complex responsible for $\beta(1\text{-}3)$-glucan formation is known to be co-localized within cortical actin patches. It moves on the cell surface to sites of cell wall remodeling, and cells with immobilized Fks1p exhibit defective cell wall structure and function. Fks1p is the product of the FKS1 gene. Echinocandins are cyclic hexapeptides N-linked to a fatty acyl side chain and inhibit the $\beta(1 \rightarrow 3)$-D-glucan synthase, which is responsible for biosynthesis of the major cell wall biopolymer. The echinocandins drugs, caspofungin, micafungin, and anidulafungin are the first of a new class of antifungal compounds that target the fungal cell wall by blocking $\beta\text{-}1,3$-glucan synthase. The safety and tolerability of caspofungin, the first approved drug, in the treatment of fungal infections have been evaluated in a number of recent studies, with no serious clinical or laboratory drug-related adverse events reported in the majority of patients.

These drugs have broad-spectrum antifungal activity against *Candida* and *Aspergillus* spp. without cross-resistance to existing antifungal agents and therefore are effective against azole-resistant yeasts and moulds. Importantly, due to their critical affect on the cell wall, echinocandins are fungicidal with yeasts. They are active against moulds, but only appear to block the growing tips of hyphae. However, they are less active against invasive *Zygomycetes, Cryptococcus neoformans*, or *Fusarium* spp. Nevertheless, they are highly effective clinically against *Aspergillus* spp. Caspofungin has been approved in the US and other countries for the treatment of a number of serious fungal infections including invasive aspergillosis in patients who are refractory to or intolerant of other therapies, esophageal candidiasis, candidemia, and other *Candida* infections (including intra-abdominal abscesses, peritonitis and pleural space infections). Caspofungin is also indicated for empirical therapy of suspected fungal infections in patients with persistent fever and neutropenia. Caspofungin is now widely used along with triazole drugs, like voriconazole, for primary antifungal therapy against yeast and moulds. The entry of the closely related drug micafungin and anidulafungin will further extend the scope of this highly efficacious new class of drugs within the clinical community.

Since the first approved echinocandin entered the market in 2002, caspofungin use in the clinic has been growing rapidly, especially as the label for caspofungin in the U.S.A. was recently expanded to include esophageal candidiasis, candidemia, and other *Candida* infections, as well as empiric therapy. Clinical isolates of *Candida* with reduced in vitro susceptibility to caspofungin have been described, and a correlation between in vivo failure and rising in vitro caspofungin MIC values has been noted, although a strict correlation between minimum inhibitory concentrations (MIC) values and clinical outcome has not yet been established. As patient exposure to caspofungin increases, and as micafungin (June 2005) and anidulafungin enter the market, it is anticipated that the number of clinical isolates with elevated MIC values will increase and an increasing number of patients will fail therapy due to reduced drug susceptibility.

This invention includes nucleic acid assays to detect mutations in fungi such as yeast of the *Candida* genus and moulds of the *Aspergillus* genus, that confer resistance to the echinocandins class of drugs, including caspofungin, micafungin and anidulafungin. The assays are suitable for any samples containing or suspected to contain the fungus, including but not limited to samples obtained from humans, for example, blood, urine or tissue samples. *Candida* species include *C. albicans, C. krusei, C. guillermondii, C. glabatra, C. tropi-* calis, and *C. parapsilosis*. *Aspergillus* species include *A. fumigatus*, *A. flavus*, *A. niger*, *A. nidulans* and *A. terreus*. Targets for the assays are nucleic acid (DNA, RNA) sequences corresponding to one or preferably, both of two conserved regions in the FKS1p family of proteins. The region that we refer to as the first region, or HS1, corresponds to the $Phe_{641}$ to $Pro_{649}$ of amino-acid sequence CaFks1p. Nucleic acid target sequences for the assays of this invention correspond to that conserved region but may correspond to one, two or a few, up to five, additional amino acids on either or both ends of each conserved region. The region that we refer to as the second region, or HS2, corresponds to $Asp_{1357}$ to $Leu_{1364}$ of amino acid sequence CaFks1p. Nucleic acid target sequences for assays of this invention correspond to that conserved region but may correspond to additional amino acids on the ends, from amino acid 1345 to the amino acid that is one, two or up to five beyond $Leu_{1364}$ of CaFks1p, for example amino acids 1345-1369. Using laboratory strains and clinical isolates we have identified a number of mutations conferring echinocandin resistance in those regions. Among the laboratory strains we have used are CAI4 and M70 (see Example 2) and laboratory mutants that we generated (designated herein as "NR" strains, for example NR2). From the laboratory strains and clinical isolates we have identified a number of single amino-acid changes that impart resistance, including F641L, F641S, S645P, S645Y, S645F, D648Y, P649H, R1361H and R1361G, and a number of SNPs responsible for the amino-acid changes.

Assays of this invention include amplification of nucleic acid sequences that include the foregoing target sequences, that is, the nucleic acid target sequences, either DNA or RNA, that correspond to, or encode, the amino acid sequences described above. Any exponential amplification method can be used, including, for example, PCR (polymerase chain reaction) (see U.S. Pat. No. 4,965,188 and published application WO 03/054233A1), LCR (the ligase chain reaction), NASBA (nucleic acid sequence based amplification), SDA (strand displacement amplification), 3SR (self-sustained sequence amplification), TMA (transcription mediated amplification), and Q-beta replicase-mediated amplification, all of which are well known in the art.

Detection of mutations in the amplified target sequences may be by any method, including but not limited to sequencing methods and detection using labeled hybridization probes. Sequencing methods include, for example, traditional dideoxy sequencing and pyrosequencing, both known in the art. Detection utilizing hybridization probes can be performed following amplification, that is, end-point detection, or in real time, that is, during the course of amplification. Real-time methods employing hybridization probes include the 5' nuclease detection method described in U.S. Pat. No. 5,487,972 and U.S. Pat. No. 5,538,848; detection utilizing molecular beacon probes described in U.S. Pat. No. 5,925,517; detection using FRET-probe pairs; detection using double-stranded probes, described in Li, Q. et al. (2002) "A New Class of Homogeneous Nucleic Acid Probes Based on Specific Displacement Hybridization," Nuc. Acid Res. 30: (2) c5); and minor grove binding (MGB) probes, described in Afonia et al. (2002) "Minor Groove Binder-Conjugated DNA Probes for Quantitative DNA Detection by Hybridization-Triggered Fluorescence," Biotechniques 32: 946-9.

Probe-detection methods of this invention utilize at least one probe that is allele-discriminating; that is, a probe that will hybridize to, and lead to signal generation from, one allele (for example, the wild-type sequence) but not another allele (for example, a mutant allele) under the detection conditions employed. Allele-discriminating probes generally have a rather short binding sequence, typically not more than 25 nucleotides in length and often 5-10 nucleotides shorter than that. Detection of drug-resistant mutants according to this invention may utilize more than one probe to interrogate an entire target sequence. Multiple probes may also be used to identify a particular mutation, that is, one probe specific for each mutation known or suspected to occur at a particular nucleotide position. Multiple-probe assays may include parallel amplifications, each containing one probe as well as assays that are partially or totally multiplexed, wherein each reaction vessel includes two or more different probes.

Assay kits according to this invention include probes and amplification primers. Generally the primers do not serve as reporter probes, but they are not prohibited from doing so. For example, so-called "scorpion" primers include attached hairpin, or molecular beacon, probes. Whitcombe et al. (1994) "Detection of PCR Products Using Self-Probing Amplicons and Fluorescence," Nat. Biotechnol. 117: 804-807. Assay kits preferably include all reagents needed for amplification and detection, at least necessary primers, probes, polymerization enzymes and dNTPs. Assay kits may include primers and probes for other purposes, for example, amplification of control oligonucleotides. Kits may also include sample preparation reagents.

This invention also includes sets of oligonucleotides that include at least primers and probes for an assay. Control oligonucleotides may optionally be included in such sets.

The details of one or more embodiments of the invention are set forth in the accompanying figures and the description below. Other features, objects, and advantages of the invention will be apparent from the description and drawings, and from the claims.

As used in this application, certain abbreviations are used.

GS is an abbreviation for glucan synthase.

Fks1p is the abbreviation for the Fks1 protein, currently ascribed as the catalytic subunit of glucan synthase complex responsible for β(1-3)-glucan formation.

FKS1 is the gene encoding Fks1p.

CaFks1p is the Fks1 protein of *C. albicans*.

CaFKS1 is the FKS1 gene of *C. albicans*.

$Ser_{645}$ is the conventional nomenclature for designating an amino acid, in this example serine, and its position in a protein. In CaFks1p, serine is amino acid number 645.

S645P designates a mutation, indicating first the amino acid of the wild type protein (in this example "S", serine); next the amino acid position (in this example "645", indicating $Ser_{645}$ as the wild-type); and finally the mutant amino acid (in this example "P", proline).

T1933C designates a gene mutation at nucleotide position 1933 from a T to a C. In the gene CaFKS1, nucleotide position 1933 occurs in the triplet coding for $Ser_{645}$ of CaFks1p, and the mutation results in an amino acid change.

SNP is the abbreviation for "single nucleotide polymorphism."

BRIEF DESCRIPTION OF THE FIGURES

FIGS. 1A and 1B set forth the gene sequence CaFKS1 (GenBank Accession number D88815), with regions wherein mutations conferring echinocandin reduced susceptibility are underlined.

FIG. 2 is the amino acid sequence CaFks1p (GenBank Accession number BAA21535), with regions wherein mutations conferring echinocandin reduced susceptibility are underlined.

FIG. 3 depicts alignment of amino acid sequence of Saccharomyces cerevisiae Fks1p with the amino acid sequence of *Candida albicans* Fks1p.

FIG. 4 sets forth sequences of primers, probes and probe targets utilized in the Examples.

FIG. 7 depicts the format for detection results of multiplex real-time assays.

DETAILED DESCRIPTION

Figure 5:
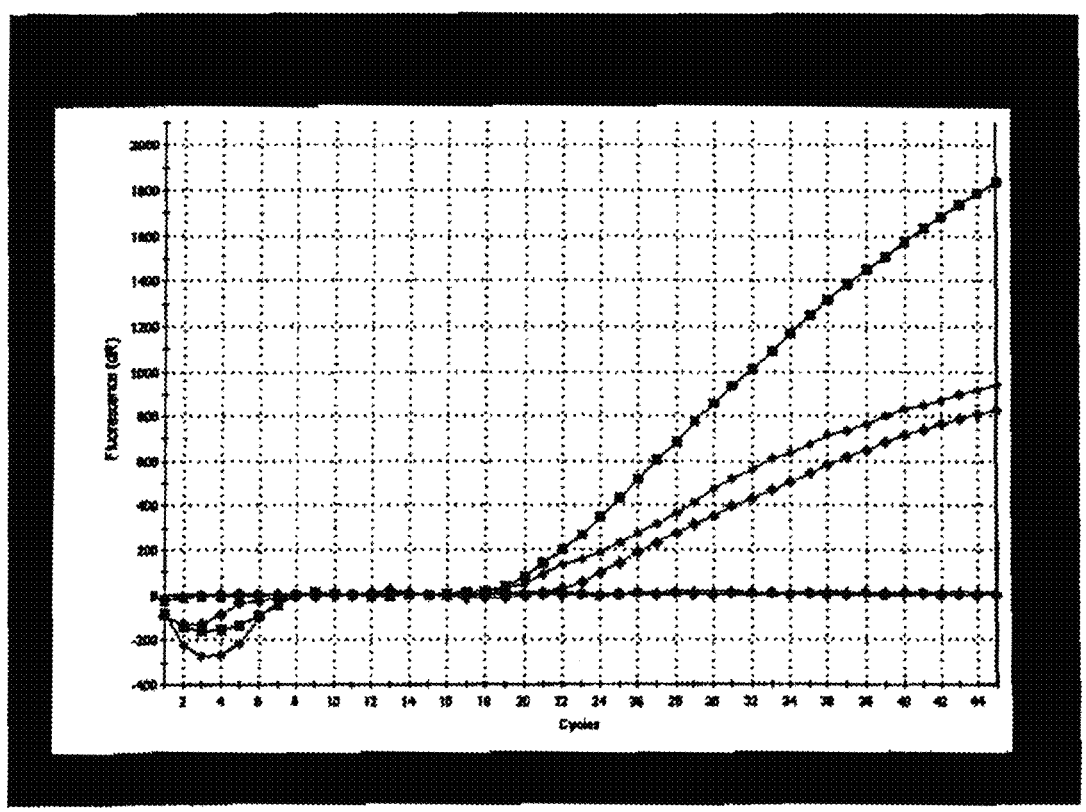
FIG. 5 is a plot of real-time PCR assays fluorescence curves from heterozygous samples.

The FKS1 gene of fungal species transcribe to corresponding messenger RNA (mRNA), which translates to the 1,3-β-D-glucan synthase (GS) subunit Fks1p. Assays according to this invention are designed to detect mutations in either or both of two short gene regions that are conserved among fungal species. Both the amino acid sequences of *Candida* and some *Aspergillus* species and their corresponding gene sequences are known.

Several sequences for CaFKS1 are available. For the design of amplification primers and probes, we relied on three: GenBank accession numbers D88815, F027295 and CA2043. FIGS. 1A and 1B present the nucleotide sequence D88815. FIG. 2 presents the amino acid sequence of CaFks1p. In FIGS. 1A and 1B the two short DNA sequences that are included in targets for assays of this invention are underlined. Those sequences for CaFKS1 span nucleotides T1921 to T1947 and G4069 to G4092. In FIG. 2 the corresponding short amino acid sequences of CaFks1p are underlined. Those sequences span F(Phe)641 to P649 and D1357 to L1364.

For locations of amino acids in different fungi producing Fks1 protein, routine alignment indicates position. FIG. 3. illustrates alignment of *C. albicans* and *S. cervisiae*. Above the line is the wild-type protein of *C. albicans*, CaFks1p, for the portion of the sequence from amino acid 641 ($Phe_{641}$) to amino acid 649 ($Pro_{649}$). That sequence closely resembles the Fks1p amino acid series of *S. cerevisiae*, but for amino acids 639 ($Phe_{639}$) to 647 ($Pro_{646}$). Below the line is the wild-type protein of *C. albicans*, CaFks1p, for the portion of the sequence from amino acid 1357 ($Asp_{1357}$) to amino acid 1364 ($Leu_{1364}$). That sequence closely resembles the Fks1p amino acid series of *S. cerevisiae*, but for amino acids 1353 ($Asp_{1353}$) to 1360 ($Leu_{1360}$). Similar alignment can be done for Fks1 proteins of other fungal species.

A description of the relevant amino acid sequence of one species is sufficient to enable persons in the art to ascertain the gene sequence corresponding to that amino acid sequence, and vise versa. Further, a description of the location of the relevant amino acid sequence of one species is sufficient to enable persons in the art to ascertain the location of the corresponding amino acid sequence of other species and, hence, the location of their corresponding gene sequences; and a description of the location of the relevant gene sequence of one species is sufficient to enable persons in the art to ascertain the location of the gene sequence in other species and from that the location of the corresponding amino acid sequences. Because we have worked primarily with *C. albicans* and *C. krusei*, the description herein is based on the *C. albicans* amino acid and gene sequences. The sequence of the FKS1 gene of *C. albicans* (CaFKS1) is GenBank Accession no D88815. The corresponding amino acid sequence of *C. albicans* (CaFks1p) is GenBank Accession no. BAA21535. Sequences of other species are: *Aspergillus fumigatus* U79728; *Aspergillus nidulans*, AACD01000061; *Candida glabrata*; CR380953; *Candida krusei*, DQ017894; *Cryptococcus neoformans*, AAEY01000070; *Paracoccidioides brasiliensis*, AF148715; *Neurospora crassa*, XM327156; *Pneumocystis carinii*, AF191096; *Saccharomyces cerevisiae* U08459; *Yarrowia lipolytica*, CR382131.

Assays of this invention are directed to the nucleic acid sequences, preferably DNA sequences, corresponding to the two short amino acid sequences underlined in FIG. 2. Regarding the first underlined sequence, the first target sequence includes DNA or RNA that encodes minimally $Phe_{641}$ through $Pro_{649}$, (using CaFks1p as the reference) and optionally from one to five additional amino acids on either or both ends, preferably one or two. Regarding the second underlined sequence, the second target sequence includes DNA or RNA that encodes minimally $Asp_{1357}$ through $Leu_{1364}$, and optionally from one to five additional amino acids on either or both ends, preferably one or two.

Assays according to this invention include amplification of a first nucleic acid region that includes the first target sequence. Preferred assays according to this invention also include amplification of a second nucleic acid region that includes the second target sequence. Both the first and second regions can be amplified using a single primer pair spanning them both. Alternatively two pairs of primers can be utilized, a first pair spanning the first region and a second pair spanning the second region. Particularly if sequencing is to be utilized for detection of mutations in the target sequences, we prefer shorter amplicons and, hence, utilization of two primer pairs. As indicated above, assays of this invention are not restricted to a particular amplification. Our work to date has utilized the polymerase chain reaction (PCR) amplification, as is reflected in the Examples, but other methods may be used.

Detection of mutations in the target sequences may be by sequencing. As reflected in the Examples, we have utilized cycle sequencing, but other sequencing methods may be used. Detection of mutations in the target sequences may also be accomplished by utilization of hybridization probes that discriminate in the assay between the wild-type target sequence and sequences that include a mutation. Hybridization probes may be DNA, RNA or a combination of the two. They may include non-natural nucleotides, for example 2'O-methyl ribonucleotides. They may include non-natural internucleotide linkages, for example, phosphorothioate linkages. They may be PNA. Hybridization probes that are useful in assays of this invention include probes whose hybridization to an allele of a target sequence leads to a detectable signal. Preferred probes are fluorescently labeled and lead to a detectable florescent signal. Detection using hybridization probes can be end-point detection, that is, detection following the completion of amplification. Preferred probe assays of this invention are homogeneous assays, that is, assays that do not require separation of bound probes from unbound probes. More preferred homogeneous assays include real-time detection, most preferably real-time fluorescence detection, that is, detection multiple times during the course of amplification. For real-time amplification assays, we prefer dual fluorescently labeled probes, most preferably probes labeled with a fluorophore and also with a non-fluorescent quencher such as 4-(4'-dimethylamino-phenylazo)benzoic acid (DABCYL).

Any suitable probing method may be utilized for real-time assays, including methods that utilize hybridization probes in combination with DNA fluorescent dyes, such as SYBR dyes, that fluoresce in the presence of double-stranded DNA. For example, SYBR Green dye may be used to detect amplification, and an allele-discriminating fluorescent hybridization probe may be used to detect the amplification of a wild-type target sequence, with the slope of probe fluorescence indicating the presence of homozygous wild-type target, heterozygosity with mutant and wild-type target, or homozygous mutant target. Another approach would be to utilize a mismatch-tolerant probe to detect one strand of amplified target sequence (whether wild-type or mutant) and allele-specific probe or probes that are hybridizable to the other strand to determine whether or not the target sequence is mutated. Alternatively, multiple probes can be utilized to signal the presence of wild-type target sequence and specific mutations as is demonstrated in the Examples. We have identified several mutations in the first and second target sequences that result in caspofungin reduced susceptibility. In the first target sequence these are (using CaFKS1 as the reference) T1921C, T1922C, G1932T, T1933C, C1934A, C1934T, C1934G, G1942T and C1946A In the second target sequence these are (using CaFKS1 as the reference) C4081G and G4082A.

A wide range of molecular methods for mutation analysis and SNP genotyping are available. Among them, Real-time PCR with detection by self reporting molecular beacon probes represents a powerful approach. Due to their hairpin structure, thermodynamically conditioned equilibrium between intra- and inter-molecular hybridization allows molecular beacon probes to be designed to distinguish closely related target sequences with higher specificity and at wider temperature range comparing with corresponding linear probes. The discriminative power of molecular beacons has been successfully applied for analysis of mutations resulting in antibiotic resistance, allele differentiation, both homozygous and heterozygous SNPs, as well as for number of other applications.

The selectivity of molecular beacon probes was useful for analysis of CaFKS1 alleles conferring reduced susceptibility to caspofungin. The assay for the first target sequence, which we have designated the "HS1" sequence, focused on CaFKS1 codon 645 mutations T1933C, C1934A and C1934T, which have been identified with clinical isolates of *C. albicans* showing reduced susceptibility to caspofungin. The design of allele-specific probes for detecting resistance alleles in the target region was complicated by the fact that a SNP, T1929A, was located within this domain. To accommodate this SNP, which appears in a large proportion of clinical isolates, the probes were designed with a wobble base at the position corresponding to SNP. Introduction of the wobble base into the probe decreased the overall fluorescence output, since at the given conditions only half of probe molecular pool would bind specifically to the complementary target DNA. Nevertheless the gain from the higher versatility of degenerate probes far exceeded the loss of absolute fluorescence intensity since such probes were reactive for entire *C. albicans* population regardless of either presence or absence of T1929A SNP in CaFKS1.

Four degenerate molecular beacons corresponding to one wild type and three mutant CaFKS1 alleles were synthesized and all four probes showed excellent discrimination characteristics with match-to-mismatch signal ratio close to 100% for most targets. Only specific hybridization with complementary DNA targets was observed for all four probes. The only exception was a minor hybridization of molecular beacon CaFKS1-WT with the template containing the T1922C allele. This result can be explained by the lateral location of the mismatch in the probe domain as well as by the energetics of forming T•G mismatch, which is known to be a relatively stable DNA-DNA mismatch pairing. In the case of allele heterozygosity, the molecular beacon probes (recognizing wild type and mutant sequences) produced fluorescent signals one-half the magnitude compared with homozygous templates.

The generation of mutants with reduced susceptibility to caspofungin was a rare event and was consistent with a mutation frequency $<10^{-8}$ mutants per viable cell. Formation of the resistant mutants required prolonged (>7 days) incubation on solid media containing caspofungin where residual cell growth occurred. We have never observed caspofungin resistant cells among *C. albicans* cultures not previously exposed to drug. Eight-five spontaneous reduced susceptibility mutants from two different strains were analyzed by the allele-specific molecular beacons. Mutations found in 35 isolates of strain CAI4 were identical to previously described substitutions affecting the codon for $Ser_{645}$. Such mutations also comprised a majority of the 50 caspofungin resistant derivatives of strain M70. Three new mutations, namely T1922C, G1932T and C1934G, affecting codons for $Phe_{641}$, $Leu_{644}$ and $Ser_{645}$ were detected in 6 strains of the spontaneous mutants derived from M70. These results are consistent with a recent mutational analysis of laboratory and clinical strains of *C. albicans* with reduced susceptibility to caspofungin. The vast majority of nucleotide substitutions were found in codon 645 of CaFKS1. The newly discovered mutations in other sites of CaFKS1 were found in progeny of only strain M70, and their relative frequency did not exceed 12%.

Overall, the application of individual molecular beacons allowed genotyping of all 85 caspofungin resistant derivatives. The three alleles targeted by molecular beacons were correctly identified in 79 strains, which was confirmed by DNA sequence analysis. The three new mutations not targeted by the molecular beacons in 6 strains were also confirmed by DNA sequence analysis. Multiplexing of all four molecular beacons in a single reaction produced universal closed tube assay for detection of caspofungin resistance mutations in the first target sequence of CaFKS1. In such assay FAM signal showed the presence of wild type CaFKS1 allele, whereas HEX fluorescence reported the presence of one of T1933C, C1934A or C1934T CaFKS1 mutations in DNA sample. DNA extracted from *C. albicans* strains heterozygous on any of above three mutations yielded both FAM and HEX signals. Thus the assay allowed for confident detection of known mutations in *C. albicans* CaFKS1 gene conferring reduced susceptibility to caspofungin in both homozygous and heterozygous state. The assay was also sensitive enough to identify other mutations in the region that can influence drug susceptibility.

As stated above, we shown that mutations linked to reduced susceptibility to caspofungin map to a short conserved regions in CaFKS1. The most prominent locus is $Ser_{645}$ and includes substitutions S645P, S645Y, S645F, which were found in both laboratory and clinical isolates of *C. albicans*. The mutations appeared to be dominant and conferred high level of caspofungin resistance in both heterozygous and homozygous state. Diagnostic probes that target such mutations can provide a rapid and accurate tool for assessment of resistance to caspofungin in *C. albicans*.

Rapid-diagnostics of caspofungin-resistance based on analysis of FKS1 mutations must have an ability to discriminate both heterozygous and homozygous alleles differing in single nucleotide as well as ability of simultaneous detection of such alleles in multiplex format. Molecular beacons technology represents an excellent technique for both allele discrimination and multiplex detection.

DNA sequence analysis of CaFKS1 from more than fifty clinical and laboratory *C. albicans* isolates with reduced susceptibility to caspofungin revealed three mutations, T1933C, C1934A and C1934T resulting in amino acid changes S645P, S645Y and S645F, respectively. Beside those nucleotide substitutions, alignment of sequencing data disclosed another point of variability in this region. In about 25% of all analyzed *C. albicans* strains, a T1929A single synonymous nucleotide substitution was observed, which was also reported in strain SC5314, as part of the *Candida albicans* genome sequencing project. This observation is significant because it has the potential to alter probe-amplicon hybridization necessary for discrimination by allele-specific probes that cover this region. Based on the CaFKS1 sequences consensus data, we designed four allele-specific molecular beacon probes that covered nucleotides 1920-1944. This work is reported in detail in the Examples. One probe was complementary to the wild type (WT) CaFKS1 allele found in caspofungin-susceptible *C. albicans* strains, while three probes were complementary to mutant CaFKS1 alleles (C1934A, C1934T, T1933C) observed in caspofungin-resistant isolates. All the beacons had identical 6-nucleotide long stem domains 5'CGCGAG and CTCGCG3' and were synthesized with a wobble base A/T 50:50 at the position corresponding to the CaFKS1 SNP at the position 1929 to ensure their alignment to target sequences. Wild type molecular beacon CaFKS1-WT was labeled with FAM at 5' end, whereas three mutant beacons were labeled with HEX at 5' end. All molecular beacons had 3' end modified with DABCYL quencher. Specifics of primer and probe design are described in Example 3. The discrimination temperature window for the probes is described in Example 4. Detection was performed in the window.

Spontaneous mutants of *C. albicans* strains CAI4 and M70 resistant to caspofungin were isolated by direct selection on solid growth media containing 4 μg/ml (forty times the MIC) caspofungin. The frequency of formation of spontaneous caspofungin-resistant derivatives for both strains was $<10^{-8}$ mutants per viable cell. For both strains, the formation of rare shrunken slow-growing colonies on the plates with caspofungin was observed. The colonies were streaked on fresh plates containing the same amount of caspofungin and did not produce any growth. After prolonged incubation for more than 10 days, a small fraction of small shrunken colonies gave rise to smooth fast-growing derivatives which were able to propagate on caspofimgin-containing media after reinoculation. Only one such derivative per individual plate/culture was saved and used for further analysis. In total, 35 and 50 isolates with reduced susceptibility to caspofungin were isolated for strains CAI4 and M70, respectively. In vitro caspofungin susceptibility testing revealed elevated MIC values >16 μg/ml of caspofungin for all laboratory-derived isolates. Details of the isolation procedure are set forth in Example 2.

The preliminary sequencing of CaFKS1 gene of CAI4 and M70 strains (See Example 2) revealed the existence of T1929A SNP in the CaFKS1 gene from CAI4 and its absence in M70. Chromosomal DNA was extracted from parental strains CAI4 and M70 and their caspofungin-resistant derivatives and was used as template for real-time PCR experiments with CaFKS1 molecular beacons. FIG. 4 gives the nucleotide sequence of the various targets, both wild-type and mutant, and primers and molecular beacon probes utilized. In FIG. 4 the probe domains of the probes and the target sequences of target strands are underlined. Bases in probes and target sequence that correspond to mutations in HS1 regions of CaFKS1 are in boldface. Base positions designated W indicate an equimolar mixture of two degenerate molecular beacons differing only by A or T at that position. Each chromosomal DNA sample was subjected to four separate PCR reactions with individual molecular beacon probes representing the different reduced susceptibility alleles: The real-time PCR protocol is described in Example 5. An annealing temperature of 61° C. was applied for all reactions, which allowed excellent discrimination between different CaFKS1 alleles (see Example 4). Mutant CaFKS1 alleles were found for all 35 caspofungin-resistant derivatives of strain CAI4. A majority of them (20 isolates) had the heterozygous mutation wt/T1933C, while 15 mutants contained the homozygous mutations T1933C, C1934A or C1934T. In the case of heterozygosity at T1933C, two signals of similar magnitude from molecular beacons CaFKS1-WT and CaFKS1-T1933C resulted (FIG. 5). FIG. 5 results of four separate PCRs with individual molecular beacons and DNA targets. —■— CaFKS1-T1933C beacon+DNA of CaFKS1 allele with homozygous T1933C mutation, —◆— CaFKS1-WT beacon+DNA of CaFKS1 allele with homozygous T1933C mutation, —*— CaFKS1-T1933C beacon+DNA of CaFKS1 allele with heterozygous T1933C mutation, —◆— CaFKS1-WT beacon+DNA of CaFKS1 allele with heterozygous T1933C mutation.

Figure 6A:
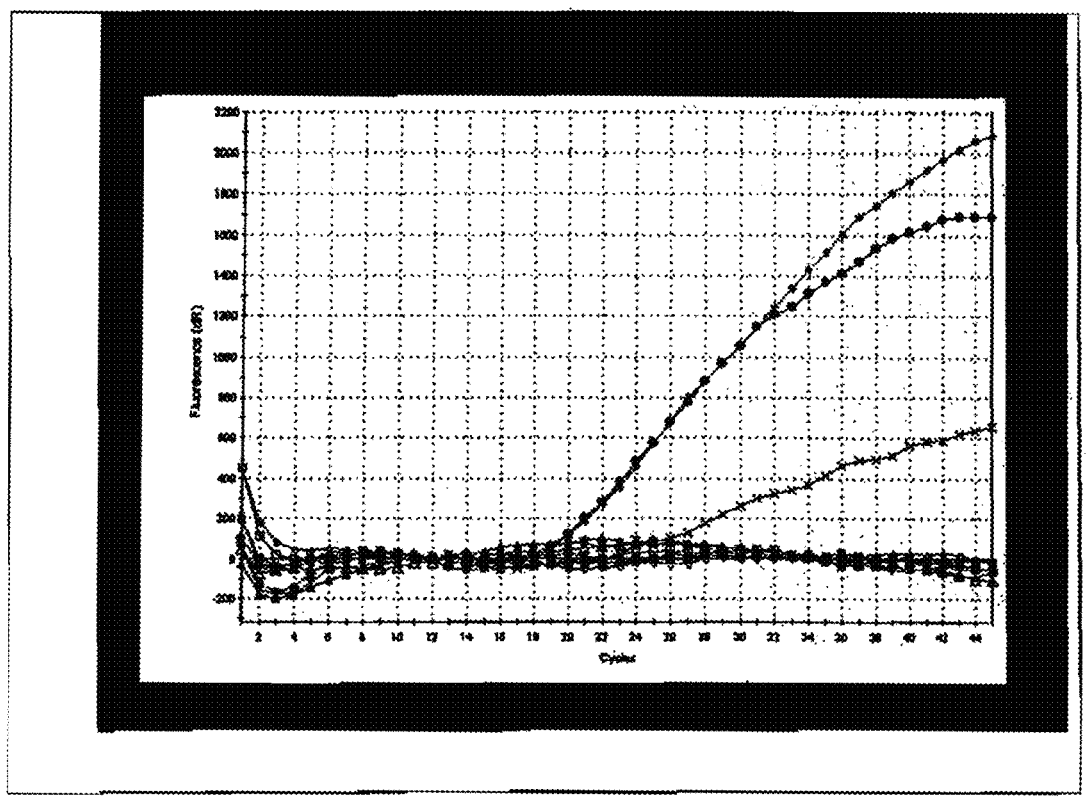
FIGS. 6A-6D are plots of real-time PCR assays fluorescence curves from homozygous samples.
Figure 6B:
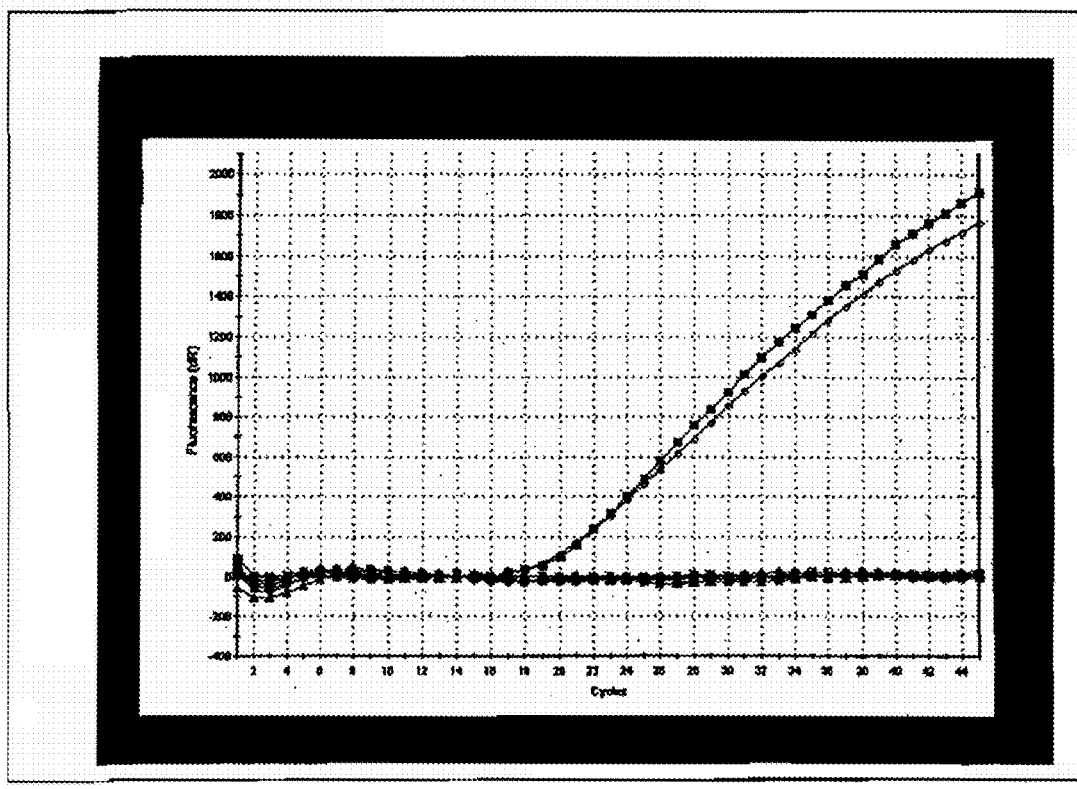
Figure 6C:
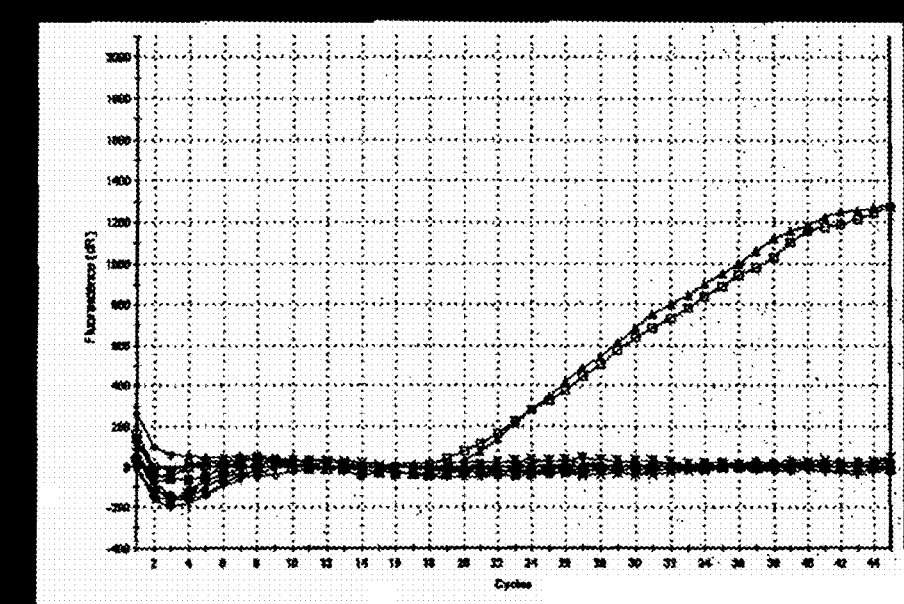
Figure 6D:
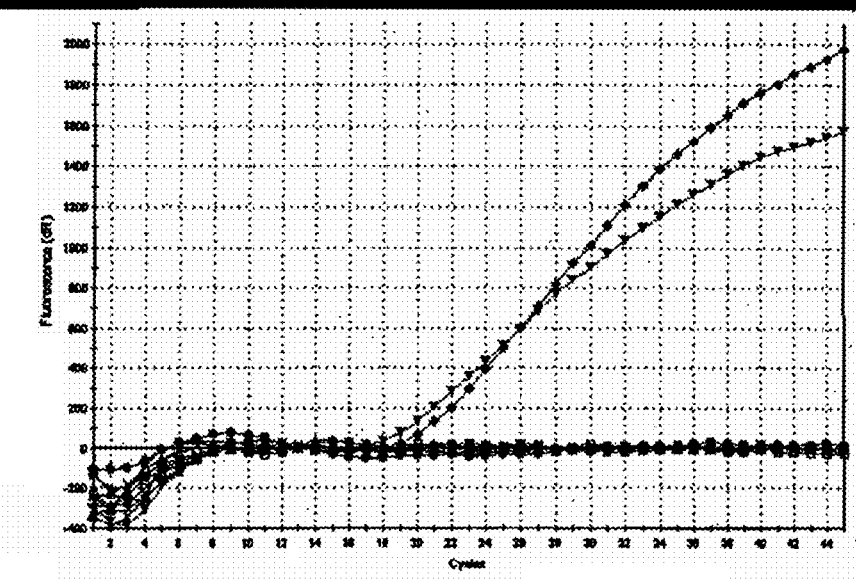

FIGS. 6A-6D show the discrimination of ten CaFKS1 homozygous alleles by four molecular beacons CaFKS1-WT (FIG. 6A), CaFKS1-T1933C (FIG. 6B), CaFKS1-C1934A (FIG. 6C) and CaFKS1-C1934T (FIG. 6D). Each plot summarizes results of eleven individual PCRs with individual DNA alleles bearing mutations: —●— wild type (no mutations or SNP), —■— T1933C, —▲— C1934A, —◆— C1934T, —*— T1929A SNP, —○— T1933C+T1929A SNP, —□— C1934A+T1929A SNP, —▼— C1934T+T1929A SNP, —✱— T1922C, —△— G1932T+C1934G, —▽— blank (no DNA).

DNA samples with homozygous CaFKS1 mutations yielded distinct responses from corresponding mutant molecular beacons with no signal from CaFKS1-WT (FIGS. 6B-6D). Conversely, chromosomal DNA from the parental strain CAI4 interacted only with the CaFKS1-WT probe while no fluorescence was detected from the mutant beacons (FIG. 6A).

Genotyping of CaFKS1 alleles of caspofungin-resistant derivatives of strain M70 revealed known mutations T1933C, C1934A or C1934T in 44 out of 50 samples. As in the case with the CAI4 mutants, a majority of M70 derivatives acquired heterozygous mutations T1933C. It was found that 25 of 50 strains with decreased susceptibility harbored the T1933C substitution in one CaFKS1 copy. Heterozygous mutations C1934A and C1934T were detected in 6 strains. All real-time PCR involving DNA samples with heterozygous mutations T1933C, C1934A or C1934T yielded two kinds of fluorescence signals from the CaFKS1-WT molecular beacon and one of the three mutant molecular beacons CaFKS1-T1933C, CaFKS1-C1934A or CaFKS1-C1934T. Beside heterozygous mutations at the positions 1933 and 1934 of CaFKS1, homozygous substitutions at these sites were also detected in 13 strains, which were identified by specific hybridization with corresponding mutant molecular beacons CaFKS1-T1933C, CaFKS1-C1934A or CaFKS1-C1934T (FIGS. 6B-6D).

In 6 of the 50 strains, PCR amplification of chromosomal DNA was only weakly detected by the wild type molecular beacon and not at all by the mutant molecular beacons (5 strains) and one strain was not detected by both wild type and mutant molecular beacons. Given the allele specificity of the probes, these data suggest that the template sequence was altered in an unknown manner.

DNA sequencing of CaFKS1 from of all caspofungin-resistant strains CAI4 and M70 was used to confirm the results of real-time PCR and to clarify the unresolved issues with six M70 derivatives. A 100% correlation between real-time PCR results and sequencing results was found for all 35 CAI4 derivatives and 44 M70 derivatives. All heterozygous and homozygous mutations detected at positions 1933 and 1934 of CaFKS1 in real-time PCR experiments by hybridization with molecular beacons CaFKS1-T1933C, CaFKS1-C1934A or CaFKS1-C1934T were confirmed by DNA sequencing. The existence of a new homozygous mutation T1922C was found in CaFKS1 gene of the five M70 derivatives which showed ambiguous results in real-time PCR experiments. Furthermore, DNA sequencing uncovered two new homozygous mutations, G1932T and C1934G, in the CaFKS1 gene of the one M70 caspofungin-resistant derivative which failed to produce any fluorescence response in real-time PCR. As expected all derivatives of strain CAI4 had T1929A SNP, whereas derivatives of strain M70 lacked it, which was revealed by sequencing.

The separate application of CaFKS1 molecular beacons made possible genotyping of three known mutations in the C. albicans CaFKS1 gene. We further investigated the possibility of combining all four degenerated CaFKS1 molecular beacons in multiplex real-time PCR format suitable for simultaneous assessment of such mutations in a given DNA sample. See Example 5. We pooled together all four CaFKS1 molecular beacons, labeled with different fluorophores for wild type and mutant, in aggregate probe mixture which was added to individual PCRs. Chromosomal DNAs from wild type strains CAI4 and M70 and 12 caspofungin resistant derivatives of these strains representing 12 different CaFKS1 genotypes were used as templates for multiplex real-time PCRs. The conditions for multiplex real-time PCR experiments were identical to those of real-time PCR with individual molecular beacons with the only exception of an annealing temperature of 60° C. The wild type molecular beacon CaFKS1-WT was labeled by FAM and mutant molecular beacons CaFKS1-T1933C, CaFKS1-C1934A or CaFKS1-C1934T were labeled by HEX. Using these probes, we were able to identify caspofungin susceptible and caspofungin resistant strains by the nature of fluorescence output.

Figure 7:
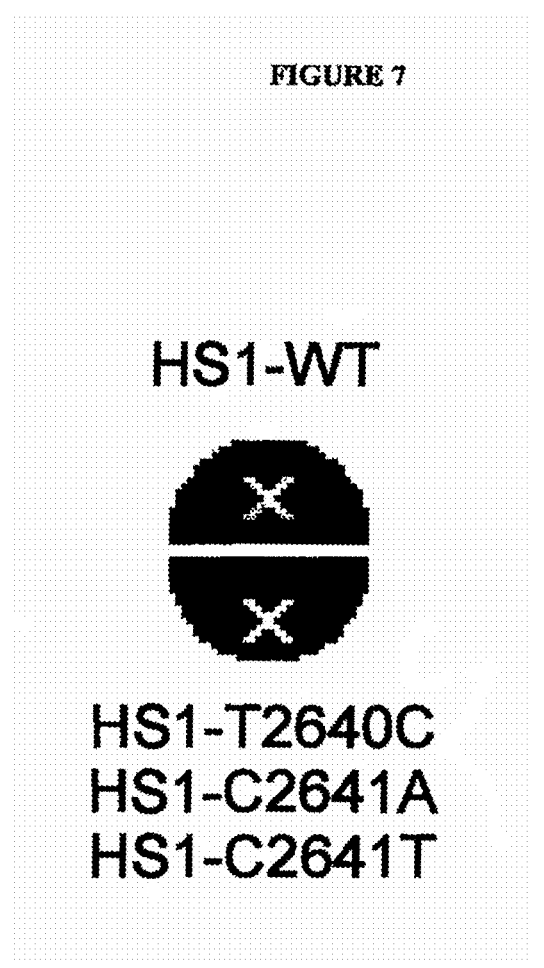

FIG. 7 illustrates the graphic output of Stratagene MX4000 software for the multiplex real-time PCR assay of CaFKS1 mutations. The top semicircle is highlighted when FAM signal is observed, reporting the presence of wild type CaFKS1 DNA. The bottom semicircle is highlighted when HEX signal is observed, reporting the presence of any of three shown mutations in CaFKS1 DNA. Homozygous CaFKS1 alleles produce either FAM or HEX signals, whereas heterozygous CaFKS1 alleles produce both FAM and HEX signals.

Only FAM fluorescence was observed when DNA from susceptible strains CAI4 and M70 was subjected to multiplex real-time PCR. Only HEX fluorescence was reported in multiplex real-time PCR with DNA bearing homozygous mutations T1933C, C1934A or C1934T in CaFKS1 (FIG. 7). Both FAM and HEX signals of equal magnitude were detected when analyzed DNA was from strains known to have heterozygous mutations T1933C, C1934A or C1934T in CaFKS1 gene (FIG. 7). Multiplex real-time PCR with chromosomal DNA from strain having two new mutations G1932T and C1934G in CaFKS1 yielded neither FAM nor HEX fluorescence. Minor FAM signals were observed in the reaction with chromosomal DNA from the strain containing a homozygous mutation T1922C.

We have also designed primers and probes for the second target region, which we refer to as "HS2," specifically for one mutant, G4082A. This is reported in Example 6. A mutant probe could be similarly designed for mutant C4081G or any other such mutant in designing assays that include the second target region, either separately or multiplexed for HS2 or for HS1 and HS2 as described in the previous Examples.

Example 1

Nucleic acid amplification of pertinent fragments of the CaFKS1 gene coupled with cycle sequencing for mutant identification has been demonstrated utilizing four different strains. Fragments of CaFKS1 (ca. 450 bp) were amplified from genomic DNA from strains CAI4-R1, NR2, NR3, and NR4. The sense and antisense primers used for PCR, based on CaFKS1 sequence (GenBank Accession no. D88815), were 5'-GAAATCGGCATATGCTGTGTC-3' (SEQ ID NO: 21) and 5'-AATGAACGACCAATGGAGAAG-3' (SEQ ID NO: 22), respectively. PCR products were cloned into pCR2.1 (Invitrogen) and the DNA sequence was determined. For clinical Candida isolates, a larger portion of the CaFKS1 ORF (ca 2.6 kb) was amplified for DNA sequence analysis using 5'-CATTGCTGTGGCCACTTTAG-3' (SEQ ID NO: 23) and 5'-GGTCAAATCAGTGAAAACCG-3' (SEQ ID NO: 24) as the forward and reverse primers, respectively. In addition to the first target region of CaFKS1 described above (corresponding to coding nucleotides 1921-1947), this fragment includes the second target nucleotides 4069-4092. The PCR products were purified, quantified by fluorescence labeling (Pico Green, Molecular Probes), and sequenced in both the 5' and 3' directions using the DTCS Quick Start Kit (Beckman Coulter).

Example 2

DNA sequence analysis using nucleic acid amplification and cycle sequencing can be used both as an assay technique in its own right and as a control to evaluate probe-based assays.

C. albicans chromosomal DNA was extracted from cells grown overnight in liquid YPD medium with Q-Biogene FastDNA kit (Q-Biogene, Irvine, Calif.). PCR experiments were performed on an iCycler thermocycler (Bio-Rad Laboratories, Hercules, Calif.). The CaFKS1 region denominated HS1 was amplified using primers CaFKS1-F1719 and CaFKS1-R2212 (FIG. 4). Each 100-μl PCR reaction contained 0.25 μM of each primer, 2.5 U of iTaq DNA polymerase (Bio-Rad Laboratories, Hercules, Calif.), 0.5 mM dNTPs, 50 mM KCl, 4 mM $MgCl_2$, 20 mM Tris-HCl, pH=8.4 and about 50 ng of C. albicans chromosomal DNA. The cycling conditions were 1 cycle of 3 min at 95° C., 35 cycles of 30 s at 95° C., 30 s at 55° C., 1 min at 72° C. 1 cycle of 3 min at 72° C. PCR products were purified using the Montage PCR purification kit (Millipore, Bedford, Mass.). PCR products for sequencing were obtained and purified using CEQ™ Dye Terminator Cycle Sequencing Quick Start kit (Beckman Coulter, Fullerton, Calif.) according to manufacturer recommendations on iCycler thermal cycler. Primers CaFKS1-F1719 or CaFKS1-R2212 were used for the sequencing reaction. The cycling conditions for sequencing PCR were 1 cycle of 3 min at 95° C., 30 cycles of 20 s at 96° C., 20 s at 50° C., 1 min at 60° C. All DNA sequencing was performed on CEQ™ 8000 Genetic Analysis System (Beckman Coulter, Fullerton, Calif.). CEQ™ 8000 Genetic Analysis System Software (Beckman Coulter, Fullerton, Calif.) was used for hardware control as well as for post run sequencing results analysis.

C. albicans strain CAI4 was purchased from ATCC (ATCC, Manassas, Va.). C. albicans strain M70 was from the Merck culture collection (MRL, Rahway, N.J.). Strains were grown on yeast extract-peptone-dextrose (YPD) medium (1% yeast extract, 2% Bacto Peptone, 2% dextrose). For growth of strain CAI4; YPD medium was supplemented by uridine (Sigma-Aldrich, St. Louis, Mo.) at 25 mg/ml. Caspofungin (Merck, Rahway, N.J.) was added directly to YPD at 4 μg/ml. Agar plates were incubated at 30° C. and liquid cultures were grown in 12-ml culture tubes containing 3 ml of YPD on the rotary shaker (100 rpm) at 30° C. Susceptibility to caspofungin was estimated in liquid microbroth dilution assay in RPMI-1640 medium (Sigma-Aldrich, St. Louis, Mo.), as outlined in NCCLS document M27-A2.

Spontaneous caspofungin-resistant mutants of *C. albicans* strains CAI4 and M70 were isolated by plating 100 ul (~$10^8$ cells) of an 18 h liquid YPD culture on YPD plates containing 4 μg/ml caspofungin. Serial dilutions of the overnight cultures were plated on the YPD plates without antibiotic selection to precisely determine starting colony counts. Selection plates were incubated for 10-14 days at 30° C. From each selection plate, at least 4 individual colonies resistant to drug were reinoculated on fresh caspofungin-containing plates to confirm the resistant phenotype.

Example 3

Three reported DNA sequences CaFKS1 GenBank accession numbers D88815 and AF027295 and CA2043) were used for FKS1 molecular beacons and primers design. Design of primers and probes for assays in known in the art. Numerous publications are available to assist researchers. Additionally, computer software packages are available to speed the process and reduce adjustments that need to be made by trial and error (see Example 4). We used such a software package. Molecular beacons and DNA primers (FIG. 4) were designed using Beacon Designer 3.0 software (PREMIER Biosoft, Palo Alto, Calif.). The default software parameters were applied for all molecular beacons and primers construction. Molecular beacons were labeled with fluorophores 5-carboxyfluorescein (FAM) and 6-carboxy-2',4,4',5',7,7'-hexachlorofluorescein (HEX) at the 5' end and with dabcyl at the 3' end. Both molecular beacons and primers were purchased from Biosearch Technologies (Biosearch Technologies, Novato, Calif.). Hybridization properties for the CaFKS1 allele specific molecular beacons were tested for the full temperature range, 25° C.-95° C., with single-stranded target oligonucleotides (FIG. 4). Molecular beacon-target hybridization was performed with the Stratagene MX4000 Multiplex Quantitative PCR system (Stratagene, La Jolla, Calif.). The "Molecular Beacon Melting Curve" experiment type was chosen in the MX4000 software for data monitoring and analysis. Each 50-μl hybridization reaction mixture contained 1× Stratagene Core PCR buffer, 4 mM $M_gCl_2$, 100 pmol of individual target oligonucleotide and 5 pmol of molecular beacon. The thermal conditions of experiment comprised heating at 95° C. for 3 minutes and cooling to 80° C. with subsequent cooling down to 25° C. using 112, 30-seconds steps with a temperature gradient –0.5° C. Fluorescence output for each individual reaction was measured at the end of the cooling step. The final data of the "Molecular Beacon Melting Curve" experiment were converted to a "SYBR Green (with Dissociation. Curve)" type of experiment. Melting temperature ($T_m$) for each molecular beacon-target pair was determined by MX4000 software as a temperature point corresponding to maximal value of the first derivative of the fluorescence output –R'(T). Each thermal profiling experiment was performed in triplicate.

Example 4

The ability of nucleic acid hybridization probes to discriminate between or among alleles is temperature-dependent; that is, if a probe discriminates against a sequence differing from target by one nucleotide at 70° C., it probably will bind to mismatched targets at 40° C. and not discriminate at such a lowered temperature.

We analyzed the allele-discriminating capability of probes as part of the probe design and assay design. Hybridization profiles were determined for molecular beacons probes against eight DNA oligonucleotide templates representing the wild-type CaFKS1 and different CaFKS1 alleles bearing caspofungin resistance mutations at positions 1933 and 1934, as well as the SNP at position 1929 (FIG. 4). The oligonucleotides described as "target" in FIG. 4 were used for melt-curve analysis of the probes. In the several target sequences, the underlined portions are complementary to one probe, as indicated, additional terminal repetitive adenosines were added to reduce secondary structure formation during melt-curve analysis. First, the hybridization of each of molecular beacon probe was assessed with two DNA targets complimentary to the probe domain sequence, which varied in the nucleotide base counterpart to the SNP at the position 1929. Each degenerate molecular beacon probe formed two types of intermolecular hybrids with such DNA targets. Stable hybrids were formed by the target oligonucleotide and a subpopulation of molecular beacon with complimentary sequence. Another subpopulation of molecular beacon probes having a single mismatched nucleotide at position 1929 formed less stable hybrid with same DNA target. As a consequence, the melting curves for the mixed probes represented as first derivative of the fluorescence output (–R'(T)) showed two distinct peaks corresponding to $T_m$s for more stable and less stable molecular beacon-target hybrids. Next we investigated the hybridization of each of molecular beacons with non-complementary DNA oligonucleotides (FIG. 4). Whereas such mismatched hybrids were generally less stable than complement, the degeneracy of molecular beacons produced the same trend for the two hybrid subpopulations. More stable intermolecular hybrids were formed by the target oligonucleotide and beacon subpopulation with single mismatch, whereas less stable hybrids comprised oligonucleotide and beacon subpopulation with double mismatches. Out of two $T_m$ values obtained for each of eight pairs of degenerated molecular beacons and target oligonucleotides only higher $T_m$ value corresponding to more stable beacon-target hybrid with one or no mismatches was taken into account. The $T_m$ values for CaFKS1 molecular beacons and their complementary DNA targets were quite close to each other and fall down to the temperature range 62.7-64.0° C. The corresponding windows of discrimination occupy the similar thermal diapason as well. Such uniformity was achieved by varying the length of the probe domain sequence for individual beacons. Molecular beacon CaFKS1-WT, CaFKS1-T1933C, CaFKS1-C1934A and CaFKS1-C1934T had probe domains of 24, 23, 25 and 25 nucleotides long correspondingly.

Example 5

A real-time amplification assay was demonstrated for the primers and probes described in FIG. 4. The assay included DNA amplification by the polymerase chain reaction (PCR) with real-time detection utilizing molecular beacon probes.

For assays employing each single probe (FIG. 4), the procedure was as follows. Real-time PCR experiments were performed on a Stratagene Mx4000 Multiplex Quantitative PCR System using the "Quantitative PCR (Multiple Standards)" setting. Reagents from Brilliant® QPCR Core Reagent kit (Stratagene, La Jolla, Calif.) were used for all reactions. Each 50-µl PCR reaction contained 1× Stratagene Core PCR buffer, 0.2 µM of molecular beacon, 0.25 µM of each of the HS1AN2 and HS1SN2 primers (FIG. 4), 2.5 U of SureStart® Taq DNA polymerase (Stratagene, La Jolla, Calif.), 0.4 mM dNTPs, 4 mM MgCl$_2$ and about 50 ng of *C. albicans* chromosomal DNA. In multiplex PCR experiments, the concentration of each of the four molecular beacons (FIG. 4) was 0.2 µM. Real-time PCR thermal cycler parameters were: 1 cycle of 10 min at 95° C., 45 cycles of 30 s at 95° C., 30 s at 61° C. and 30 s at 72° C. An annealing temperature of 60° C. was used when PCR experiments were performed in multiplex format. The filter gain set of the Mx4000 System was changed to FAM-960 HEX-720 with an aim of equalization of the fluorescence signal magnitudes from different molecular beacons. The fluorescence was measured 3 times during the annealing step.

Fluorescence signals coming from Stratagene Mx4000 System during PCR amplification were monitored using Mx4000 software in real time. At the end of each run, the amplification plots data were converted to graphic format and stored as image files or exported into Microsoft Office Excel and stored as spreadsheet files. In the case of multiplex PCR reactions, the final results of PCR amplifications were converted from a "Quantitative PCR (Multiple Standards)" type of experiment to the "Quantitative Plate Read" type of experiment. Total changes in fluorescence for individual fluorophores (Rpost-Rpre) were taken as values for analysis. Results were converted to graphic or numerical format and stored as image or spreadsheet files.

For multiplex assays we utilized PCR amplification as described above, except that the annealing temperature of the thermal cycles was 60° C. rather than 61° C. Multiple probes were utilized in the same reaction.

Example 6

Primers and molecular beacon probes for PCR amplification assays have been designed for the second DNA sequence, which we refer to as HS2. The primers have the following sequences:

```
                                     (SEQ ID NO: 25)
CCATTTGGTTGTTACAATATTGC-3'

(SEQ ID NO: 26)
CCAATGGAATGAAAGAAATGAAG-3'.
```

To distinguish the wild-type gene sequence from the echinocandin-resistant mutant G4082A, the nucleotide sequences for a pair of allele-discriminating molecular probes was designed. Each would be labeled at one end with a fluorophore and at the other end with a non-fluorescent quencher such as DABCYL. Of course, differentiable fluorophores would be utilized such that the wild-type probe would hybridize only to the wild-type gene sequence and thereupon fluoresce, and the mutant probe would hybridize only to the mutant sequence and thereupon fluoresce in end-point assays and real-time amplifications containing one of these probes, or in multiplexed assays containing both probes, with or without primers and probes for the first target sequence.

The molecular beacon probes have single-stranded loops that are 24 nucleotides in length flanked by complementary 3' and 5' arm sequences that form a 6-nucleotide stem. Both probes have a calculated T$_m$ of 61.5° C. Their sequences are:

```
                                     (SEQ ID NO: 27)
Wild-type probe:
CGCGAGGATTGGATTAGACGTTATACTTTGCTCGCG (SEQ ID NO: 28)
Mutant probe:
CGCGAGGATTGGATTAGACATTATACTTTGCTCGCG.
```

Where the complementary arms are underlined and the single nucleotide changed in the mutant is bolded.

A number of embodiments of the invention have been described. Nevertheless, it will be understood that various modifications may be made without departing from the spirit and scope of the invention. For example, amplification methods other than PCR can be used, for example NASBA, and allele-discriminating probes other than molecular beacon probes can be used. Accordingly, other embodiments are within the scope of the following claims.

What is claimed is:

1. A nucleic acid assay for detecting echinocandin drug resistance mutations in fungi susceptible to echinocandin drugs and containing the FKS1 gene corresponding to 1-3β-D-glucan synthase subunit Fks1p comprising exponentially amplifying a first nucleic acid target sequence of the FKS1 gene corresponding to at least a portion of CaFks1p amino acids 636 to 654 that includes amino acids 641 to 649 to generate an amplified first target sequence, contacting the amplified first target sequence with a first labeled hybridization probe specific for an amino acid mutation selected from the group consisting of S645P, S645Y, and S645F of CaFks1p, and detecting the presence of the mutation, thereby detecting an echinocandin drug resistance mutation.

2. The assay of claim 1 wherein the fungi are a *Candida* species.

3. The assay of claim 1, further comprising contacting the amplified first target sequence with an additional labeled hybridization probe specific for at least one amino acid mutation selected from the group consisting of F641L, F641S, D648Y and P649H of CaFks1p.

4. The assay according to claim 1 wherein the step of amplifying includes amplifying a second nucleic acid target sequence of the FKS1 gene corresponding to 1-3-β-D-glucan synthase subunit Fks 1 p corresponding to at least a portion of CaFks1p amino acids 1345 to 1369 that includes amino acids 1357 to 1364 to generate an amplified second target sequence, and wherein the step of detecting includes detecting any difference from the wild-type allele in said amplified second target sequence.

5. The assay of claim 4 that is capable of detecting at least one amino acid change selected from the group consisting of R1361H and R1361G of CaFks1p.

6. The assay of claim 4 wherein amplification of the first target sequence and the second target sequence are performed in the same reaction mixture.

7. The assay of claim 1 wherein the step of detecting further comprises sequencing.

8. The assay of claim 4 wherein the step of detecting comprises contacting the amplified second target sequence with a second labeled hybridization probe specific for at least one amino acid mutation selected from the group consisting of R1361H and R1361G of CaFks1p.

9. The assay of claim 8 wherein detection is homogeneous end-point or real-time detection.

10. The assay according to claim 9, wherein the detection is a real-time detection.

11. The assay according to claim 1 wherein the step of amplifying includes an amplification method selected from the group consisting of PCR, NASBA and TMA.

12. The assay of claim 1, wherein the amplifying step is conducted in a sample obtained from a human or from a clinical isolate.

* * * * *

SEQUENCE LISTING

<160> NUMBER OF SEQ ID NOS: 28

<210> SEQ ID NO 1
<211> LENGTH: 6473
<212> TYPE: DNA
<213> ORGANISM: Candida albicans

<400> SEQUENCE: 1

| gaattctaaa | attagcaaaa | aaaaattgtg | tgtgcgtgtg | agttggtaaa | agaaacgaaa | 60 |
| aaaaagcaat | ttttacattt | gctatcttca | gttttaaggc | atttgattac | ccaatttgaa | 120 |
| ataagtccaa | aagatatcca | tttaaaacaa | acagtatttc | ctgtatttat | caatttatca | 180 |
| aagaatctag | cattcatata | taatcaatct | aacttcttgg | tgtttaagaa | atcctcctac | 240 |
| tactcacaaa | tctcgagcaa | aatttttttt | ttgtttgatc | tcatacgatt | tcaggtacaa | 300 |
| ttttttttaaa | aggaaaaagt | ttgcaatatc | ttacataatt | tggattgctg | tttttattat | 360 |
| agggtcagat | tcacatttcc | agatctcaat | agaaacccag | tttcccatta | atttaagaga | 420 |
| tatcagttta | tttcgattac | aaattgagtt | gtcacaacta | cgtttcacat | atactattat | 480 |
| ttcaatttcc | catcattgca | acaacaaacg | aaaaattaat | tcttgatttt | gctgttttttt | 540 |

```
tttgtgaaca aaaagcacac aaacatacac acaatacatt taataacaac aattttcaaa    600
ataataataa cttttcctt tctttaat ttccccct ctttttt aaatattaaa    660 aaccaacacc caactgatat actaacttat ctttttttc aaattagatg tcgtataacg    720
ataataataa tcattattac gaccctaatc aacagggcgg tatgccacct catcaaggag    780
gagaagggta ttaccaacaa cagtatgatg atatgggtca acaaccacac caacaagatt    840
attacgatcc aaatgctcaa tatcaacaac aaccatatga catggatgga tatcaagacc    900
aagccaacta tggtggtcaa ccaatgaatg cccagggtta taatgctgac ccagaagcct    960
tttctgactt tagttatggt ggtcaaactc ctggaactcc tggttatgat caatacggta   1020
ctcaatacac cccatctcaa atgagttatg gtggtgatcc aagatcttct ggtgcttcaa   1080 caccaatttta tggtggtcaa ggtcaaggtt acgatccaac tcaattcaat atgtcatcga   1140
acttgccata tccagcttgg tctgctgatc ctcaagctcc aattaagatt gaacacatcg   1200
aagatatttt cattgatttg actaataaat ttggtttcca aagagattct atgagaaaca   1260
tgtttgatta ctttatgaca ttgttggact cgagatcttc ccgtatgtca ccagctcagg   1320
ccttgttgag tttacatgct gattatattg gtggtgacaa tgccaattat agaaaatggt   1380
atttttcttc acaacaagat ttggatgatt ccttaggttt tgctaatatg actttaggta   1440
aaattggtag aaaagccaga aaagcttcca agaaatccaa aaaagctaga aaagctgctg   1500
aagaacatgg tcaagatgtc gatgctcttg ctaatgaatt agaaggtgat tattcattgg   1560
aagccgctga atcagatgg aaagccaaga tgaactcttt gactccagaa gaaagagtaa   1620
gagaccttgc tctttatttg ttgatatggg gtgaagccaa tcaagttcgt tttactcctg   1680
aatgtttgtg ttacatttac aaatctgcca ctgattattt aaattctcca ttgtgtcaac   1740
aaagacaaga accagtgcct gaaggtgatt acttgaaccg tgtgatcact ccactttaca   1800
gattcatcag atctcaagtt tatgaaattt atgatggaag atttgtcaag cgtgaaaaag   1860
accacaacaa ggtcattggt tatgatgatg tcaatcaatt gttttggtac ccagaaggta   1920
tttccagaat tatttttgaa gatggaacca gattggttga tatccctcaa gaagaacgtt   1980
tcttgaaatt aggtgaagtt gaatggaaga atgttttctt caaaacttat aaggaaatca   2040
gaacctggtt gcatttcgtt accaattta atagaatctg gattatccat ggtaccatct   2100
actggatgta cactgcttac aactccccaa ccttgtatac taaacattat gtccaaacca   2160
taaatcaaca accacttgct tcgtcaagat gggctgcttg tgccattggt ggtgttcttg   2220
cttcatttat tcaaattctt gccacacttt tcgaatggat tttcgtgcct agagaatggg   2280
ccggtgctca acatttgagt cgtcgtatgc tattttggt gttaattttc ttactcaatt   2340
tggttccacc agtttataca ttccaaatta ccaaattggt gatttattcg aaatcggcat   2400
atgctgtgtc gattgttgga tttttcattg ctgtggccac tttagtattc tttgccgtca   2460
tgccattggg tggtttattc acttcataca tgaacaagag atcaagaaga tatattgcat   2520
cacaaacatt tactgccaac tacattaaat tgaaaggttt agatatgtgg atgtcttatt   2580
tgttatggtt tttggttttc cttgccaaat tggttgaatc ttatttcttc tcgactttgt   2640
ctttaagaga tcctattaga aacttgtcga ccatgacaat gagatgtgtt ggtgaagttt   2700
ggtacaaaga tattgtttgt agaaaccaag ccaagattgt cttgggggttg atgtatcttg   2760 ttgatttgtt attgttcttt ttggatactt atatgtggta cattatttgt aactgtatct   2820
tctccattgg tcgttcattc tatttgggta tttccatttt gactccttgg agaaacattt   2880
tcaccagatt gccaaagaga atttattcca agattttagc taccacggaa atggaaatca   2940
```

```
aatataaacc taaagttttg atttcacaaa tttggaatgc cattgttatt tccatgtaca    3000
gagaacattt gttagccatt gatcacgttc aaaaattatt gtatcatcaa gttccatctg    3060
aaattgaagg caagagaact ttgagagctc caactttctt tgtttctcaa gatgacaaca    3120
attttgaaac ggaattttc ccaagaaatt ctgaagctga aagaagaatt tcattttcg      3180 ctcaatcttt ggctacacca atgccagaac cattaccagt tgataatatg ccaactttta    3240
ctgttttcac tcctcattat tcggaaaaga ttttgttatc tttgagagaa atcattagag    3300
aagatgatca attctcaaga gtgacattat tggaatattt gaaacaatta catccagttg    3360
aatgggattg ttttgttaag gacaccaaga ttttggctga agaaactgct gcttatgaaa    3420
atggtgatga ttctgaaaaa ttatctgaag atggattgaa atccaagatt gatgatttac    3480
cattctattg tattggtttc aagtctgccg cccctgaata tactttaaga acaagaattt    3540
gggcttcatt gagatcccaa actttgtaca gaactgtatc tgggtttatg aattatgcca    3600
gagccattaa attgttatac agagtggaaa acccagaatt ggttcaatat ttcggtggtg    3660
accctgaagg attagaatta gctttagaaa gaatggccag aagaaagttt agattttgg     3720 tttctatgca aagattgtct aaattcaaag atgatgaaat ggaaaatgct gagttcttat    3780
tgcgtgctta ccctgatttg caaattgctt acttggatga agaaccggct ttgaatgagg    3840
acgaggaacc aagagtatac tctgccttga ttgatggtca ttgtgaaatg ttagaaaatg    3900
gtagacgtcg tcctaaattc agagttcaat tgtctggtaa tccaattttg ggtgatggta    3960
aatctgataa tcaaaatcat gcggttattt tccatagagg tgaatatatt caattgattg    4020
atgctaatca agataattat ttggaagaat gtttgaagat tagatcagtt ttggctgaat    4080
ttgaagaaat gaatgttgaa catgttaatc catatgcacc aaatttgaaa tctgaagata    4140
ataacaccaa gaaggatcca gtggcatttt tgggtgctag agaatatatt ttctcagaaa    4200
attctggtgt tttgggtgat gttgctgctg gtaaagaaca aacttttggt acattgtttg    4260
caagaacttt ggcacaaatt ggaggtaaat tgcattatgg tcatccggat tttttgaatg    4320
ctacatttat gttaactaga ggtggtgttt ctaaagcaca aaagggttta catttgaatg    4380
aagatattta tgctggtatg aatgccatga tgagaggtgg taaaatcaag cattgtgaat    4440
attatcaatg tggtaaaggt agagatttag gttttggatc catttgaat ttcaccacca     4500 agattggtgc tggtatggga gaacaaatgc tttcaagaga atatttctat ttgggtactc    4560
aacttccatt ggatagattt ttgtcatttt actatggtca tccaggtttc catattaata    4620
acttgtttat tcaattgtct ttacaagtgt ttattttggt gttgggtaac ttgaattcat    4680
tagctcatga agctatcatg tgttcttaca acaaagatgt cccagttact gatgttttgt    4740
atccatttgg ttgttacaat attgctcctg ccgttgattg gattagacgt tatactttgt    4800 ctatttcat tgtttcttc atttcttca ttccattggt tgtacaagaa ttgattgaaa       4860 gagggtatg gaaagcgttc caaagatttg ttagacattt tatttccatg tcaccatttt     4920
tcgaagtttt cgttgcccaa atttattcat catcggtttt cactgatttg accgttggtg    4980
gtgctagata tatttccact ggtagaggtt ttgccacttc aagaattcca ttttcaatct    5040
tgtattcacg ttttgctgat tcatccattt atatgggagc aagattgatg ttgattttat    5100
tatttggtac agtttctcat tggcaagcac cattattatg gttctgggct tcattatcgg    5160
ctttaatgtt ctccccattc atttttcaatc ctcatcaatt tgcttgggaa gactttttcc   5220
ttgattacag agatttcatt agatggttat ctagaggtaa cactaaatgg cacagaaact    5280
catggattgg ttatgttaga ctttctagat cacgtatcac tggtttcaaa cgtaagttga    5340
```

-continued

```
ctggtgatgt tctgaaaaa gctgctggtg atgcttcaag agctcataga tccaatgttt    5400
tgtttgctga tttcttacca acattgattt atactgctgg tctttatgtt gcttatactt    5460
ttattaatgc tcaaactggg gttactagtt atccatatga aatcaatgga tctactgatc    5520
cacaaccagt taattctact ttgagactta ttatttgtgc tttagctcca gttgttattg    5580
atatgggatg tttaggtgtt tgtcttgcca tggcatgttg tgctggtcca atgttaggat    5640
tatgttgtaa aaagactggt gctgttattg ctggtgttgc ccatggtgtt gccgtcattg    5700
ttcatattat tttctttatt gttatgtggg tcactgaagg tttcaatttt gccagattaa    5760
tgttgggtat tgccaccatg atttatgttc aaagattatt attcaagttt ttgacattat    5820
gtttcttgac tagagaattt aagaatgata agccaatac tgctttctgg actggtaaat    5880
ggtataatac tggtatggga tggatggctt ttactcaacc atctcgtgaa tttgttgcta    5940
aaatcattga aatgtcggaa tttgctggtg atttcgtttt ggcacatatt atattattct    6000
gtcaattacc attattgttt attccattag ttgatagatg gcattcaatg atgttattct    6060
ggttgaaacc atcaagattg attagaccac caatttattc tttgaaacaa gccagattaa    6120
gaaagagaat ggtgagaaaa tattgtgttt tatattttgc cgtgttgata ttatttattg    6180
tcattattgt tgcaccagca gttgcttcgg gacaaattgc tgttgatcaa tttgccaata    6240
ttggtggatc tggttctatt gctgatggat tattccaacc aagaaatgtc agtaataatg    6300
atactggtaa tcatagacca aaaacctaca cttggagtta tttgagtact cgttttactg    6360
gaagtaccac cccttattct acaaatccat tcagagttta agagtttaag agattaagcg    6420
gggggcggaa gtggtttatt catttataat tatttcattt attcataaat ggt          6473
```

<210> SEQ ID NO 2
<211> LENGTH: 1897
<212> TYPE: PRT
<213> ORGANISM: Candida albicans

<400> SEQUENCE: 2

```
Met Ser Tyr Asn Asp Asn Asn His Tyr Tyr Asp Pro Asn Gln Gln
1               5                   10                  15

Gly Gly Met Pro Pro His Gln Gly Gly Glu Gly Tyr Tyr Gln Gln Gln
            20                  25                  30

Tyr Asp Asp Met Gly Gln Gln Pro His Gln Gln Asp Tyr Tyr Asp Pro
        35                  40                  45

Asn Ala Gln Tyr Gln Gln Gln Pro Tyr Asp Met Asp Gly Tyr Gln Asp
    50                  55                  60

Gln Ala Asn Tyr Gly Gly Gln Pro Met Asn Ala Gln Gly Tyr Asn Ala
65                  70                  75                  80

Asp Pro Glu Ala Phe Ser Asp Phe Ser Tyr Gly Gly Gln Thr Pro Gly
                85                  90                  95

Thr Pro Gly Tyr Asp Gln Tyr Gly Thr Gln Tyr Thr Pro Ser Gln Met
            100                 105                 110

Ser Tyr Gly Gly Asp Pro Arg Ser Ser Gly Ala Ser Thr Pro Ile Tyr
        115                 120                 125

Gly Gly Gln Gly Gln Gly Tyr Asp Pro Thr Gln Phe Asn Met Ser Ser
    130                 135                 140

Asn Leu Pro Tyr Pro Ala Trp Ser Ala Asp Pro Gln Ala Pro Ile Lys
145                 150                 155                 160

Ile Glu His Ile Glu Asp Ile Phe Ile Asp Leu Thr Asn Lys Phe Gly
                165                 170                 175
```

```
Phe Gln Arg Asp Ser Met Arg Asn Met Phe Asp Tyr Phe Met Thr Leu
            180                 185                 190

Leu Asp Ser Arg Ser Arg Met Ser Pro Ala Gln Ala Leu Leu Ser
        195                 200                 205

Leu His Ala Asp Tyr Ile Gly Gly Asp Asn Ala Asn Tyr Arg Lys Trp
    210                 215                 220

Tyr Phe Ser Ser Gln Gln Asp Leu Asp Asp Ser Leu Gly Phe Ala Asn
225                 230                 235                 240

Met Thr Leu Gly Lys Ile Gly Arg Lys Ala Arg Lys Ala Ser Lys Lys
                245                 250                 255

Ser Lys Lys Ala Arg Lys Ala Ala Glu Glu His Gly Asn Asp Val Asp
            260                 265                 270

Ala Leu Ala Asn Glu Leu Glu Gly Asp Tyr Ser Leu Glu Ala Ala Glu
        275                 280                 285

Ile Arg Trp Lys Ala Lys Met Asn Ser Leu Thr Pro Glu Glu Arg Val
    290                 295                 300

Arg Asp Leu Ala Leu Tyr Leu Leu Ile Trp Gly Glu Ala Asn Gln Val
305                 310                 315                 320

Arg Phe Thr Pro Glu Cys Leu Cys Tyr Ile Tyr Lys Ser Ala Thr Asp
                325                 330                 335

Tyr Leu Asn Ser Pro Leu Cys Gln Gln Arg Gln Glu Pro Val Pro Glu
            340                 345                 350

Gly Asp Tyr Leu Asn Arg Val Ile Thr Pro Leu Tyr Arg Phe Ile Arg
        355                 360                 365

Ser Gln Val Tyr Glu Ile Tyr Asp Gly Arg Phe Val Lys Arg Glu Lys
    370                 375                 380

Asp His Asn Lys Val Ile Gly Tyr Asp Asp Val Asn Gln Leu Phe Trp
385                 390                 395                 400

Tyr Pro Glu Gly Ile Ser Arg Ile Ile Phe Glu Asp Gly Thr Arg Leu
                405                 410                 415

Val Asp Ile Pro Gln Glu Glu Arg Phe Leu Lys Leu Gly Glu Val Glu
            420                 425                 430

Trp Lys Asn Val Phe Phe Lys Thr Tyr Lys Glu Ile Arg Thr Trp Leu
        435                 440                 445

His Phe Val Thr Asn Phe Asn Arg Ile Trp Ile Ile His Gly Thr Ile
    450                 455                 460

Tyr Trp Met Tyr Thr Ala Tyr Asn Ser Pro Thr Leu Tyr Thr Lys His
465                 470                 475                 480

Tyr Val Gln Thr Ile Asn Gln Gln Pro Leu Ala Ser Ser Arg Trp Ala
                485                 490                 495

Ala Cys Ala Ile Gly Gly Val Leu Ala Ser Phe Ile Gln Ile Leu Ala
            500                 505                 510

Thr Leu Phe Glu Trp Ile Phe Val Pro Arg Glu Trp Ala Gly Ala Gln
        515                 520                 525

His Leu Ser Arg Arg Met Leu Phe Leu Val Leu Ile Phe Leu Leu Asn
    530                 535                 540

Leu Val Pro Pro Val Tyr Thr Phe Gln Ile Thr Lys Leu Val Ile Tyr
545                 550                 555                 560

Ser Lys Ser Ala Tyr Ala Val Ser Ile Val Gly Phe Phe Ile Ala Val
                565                 570                 575

Ala Thr Leu Val Phe Phe Ala Val Met Pro Leu Gly Gly Leu Phe Thr
            580                 585                 590

Ser Tyr Met Asn Lys Arg Ser Arg Tyr Ile Ala Ser Gln Thr Phe
        595                 600                 605
```

Thr Ala Asn Tyr Ile Lys Leu Lys Gly Leu Asp Met Trp Met Ser Tyr
610             615                 620

Leu Leu Trp Phe Leu Val Phe Leu Ala Lys Leu Val Glu Ser Tyr Phe
625                 630                 635                 640

Phe Ser Thr Leu Ser Leu Arg Asp Pro Ile Arg Asn Leu Ser Thr Met
                645                 650                 655

Thr Met Arg Cys Val Gly Glu Val Trp Tyr Lys Asp Ile Val Cys Arg
            660                 665                 670

Asn Gln Ala Lys Ile Val Leu Gly Leu Met Tyr Leu Val Asp Leu Leu
        675                 680                 685

Leu Phe Phe Leu Asp Thr Tyr Met Trp Tyr Ile Ile Cys Asn Cys Ile
690                 695                 700

Phe Ser Ile Gly Arg Ser Phe Tyr Leu Gly Ile Ser Ile Leu Thr Pro
705                 710                 715                 720

Trp Arg Asn Ile Phe Thr Arg Leu Pro Lys Arg Ile Tyr Ser Lys Ile
                725                 730                 735

Leu Ala Thr Thr Glu Met Glu Ile Lys Tyr Lys Pro Lys Val Leu Ile
            740                 745                 750

Ser Gln Ile Trp Asn Ala Ile Val Ile Ser Met Tyr Arg Glu His Leu
        755                 760                 765

Leu Ala Ile Asp His Val Gln Lys Leu Leu Tyr His Gln Val Pro Ser
770                 775                 780

Glu Ile Glu Gly Lys Arg Thr Leu Arg Ala Pro Thr Phe Phe Val Ser
785                 790                 795                 800

Gln Asp Asp Asn Asn Phe Glu Thr Glu Phe Phe Pro Arg Asn Ser Glu
                805                 810                 815

Ala Glu Arg Arg Ile Ser Phe Phe Ala Gln Ser Leu Ala Thr Pro Met
            820                 825                 830

Pro Glu Pro Leu Pro Val Asp Asn Met Pro Thr Phe Thr Val Phe Thr
        835                 840                 845

Pro His Tyr Ser Glu Lys Ile Leu Leu Ser Leu Arg Glu Ile Ile Arg
850                 855                 860

Glu Asp Asp Gln Phe Ser Arg Val Thr Leu Leu Glu Tyr Leu Lys Gln
865                 870                 875                 880

Leu His Pro Val Glu Trp Asp Cys Phe Val Lys Asp Thr Lys Ile Leu
                885                 890                 895

Ala Glu Glu Thr Ala Ala Tyr Glu Asn Gly Asp Asp Ser Glu Lys Leu
            900                 905                 910

Ser Glu Asp Gly Leu Lys Ser Lys Ile Asp Asp Leu Pro Phe Tyr Cys
        915                 920                 925

Ile Gly Phe Lys Ser Ala Ala Pro Glu Tyr Thr Leu Arg Thr Arg Ile
930                 935                 940

Trp Ala Ser Leu Arg Ser Gln Thr Leu Tyr Arg Thr Val Ser Gly Phe
945                 950                 955                 960

Met Asn Tyr Ala Arg Ala Ile Lys Leu Leu Tyr Arg Val Glu Asn Pro
                965                 970                 975

Glu Leu Val Gln Tyr Phe Gly Gly Asp Pro Glu Gly Leu Glu Leu Ala
            980                 985                 990

Leu Glu Arg Met Ala Arg Arg Lys Phe Arg Phe Leu Val Ser Met Gln
        995                 1000                1005

Arg Leu Ser Lys Phe Lys Asp Asp Glu Met Glu Asn Ala Glu Phe
        1010                1015                1020

Leu Leu Arg Ala Tyr Pro Asp Leu Gln Ile Ala Tyr Leu Asp Glu

-continued

```
            1025                1030                1035

Glu  Pro  Ala  Leu  Asn  Glu  Asp  Glu  Glu  Pro  Arg  Val  Tyr  Ser  Ala
     1040                1045                1050

Leu  Ile  Asp  Gly  His  Cys  Glu  Met  Leu  Glu  Asn  Gly  Arg  Arg  Arg
     1055                1060                1065

Pro  Lys  Phe  Arg  Val  Gln  Leu  Ser  Gly  Asn  Pro  Ile  Leu  Gly  Asp
     1070                1075                1080

Gly  Lys  Ser  Asp  Asn  Gln  Asn  His  Ala  Val  Ile  Phe  His  Arg  Gly
     1085                1090                1095

Glu  Tyr  Ile  Gln  Leu  Ile  Asp  Ala  Asn  Gln  Asp  Asn  Tyr  Leu  Glu
     1100                1105                1110

Glu  Cys  Leu  Lys  Ile  Arg  Ser  Val  Leu  Ala  Glu  Phe  Glu  Glu  Met
     1115                1120                1125

Asn  Val  Glu  His  Val  Asn  Pro  Tyr  Ala  Pro  Asn  Leu  Lys  Ser  Glu
     1130                1135                1140

Asp  Asn  Asn  Thr  Lys  Lys  Asp  Pro  Val  Ala  Phe  Leu  Gly  Ala  Arg
     1145                1150                1155

Glu  Tyr  Ile  Phe  Ser  Glu  Asn  Ser  Gly  Val  Leu  Gly  Asp  Val  Ala
     1160                1165                1170

Ala  Gly  Lys  Glu  Gln  Thr  Phe  Gly  Thr  Leu  Phe  Ala  Arg  Thr  Leu
     1175                1180                1185

Ala  Gln  Ile  Gly  Gly  Lys  Leu  His  Tyr  Gly  His  Pro  Asp  Phe  Leu
     1190                1195                1200

Asn  Ala  Thr  Phe  Met  Leu  Thr  Arg  Gly  Gly  Val  Ser  Lys  Ala  Gln
     1205                1210                1215

Lys  Gly  Leu  His  Leu  Asn  Glu  Asp  Ile  Tyr  Ala  Gly  Met  Asn  Ala
     1220                1225                1230

Met  Met  Arg  Gly  Gly  Lys  Ile  Lys  His  Cys  Glu  Tyr  Tyr  Gln  Cys
     1235                1240                1245

Gly  Lys  Gly  Arg  Asp  Leu  Gly  Phe  Gly  Ser  Ile  Leu  Asn  Phe  Thr
     1250                1255                1260

Thr  Lys  Ile  Gly  Ala  Gly  Met  Gly  Glu  Gln  Met  Leu  Ser  Arg  Glu
     1265                1270                1275

Tyr  Phe  Tyr  Leu  Gly  Thr  Gln  Leu  Pro  Leu  Asp  Arg  Phe  Leu  Ser
     1280                1285                1290

Phe  Tyr  Tyr  Gly  His  Pro  Gly  Phe  His  Ile  Asn  Asn  Leu  Phe  Ile
     1295                1300                1305

Gln  Leu  Ser  Leu  Gln  Val  Phe  Ile  Leu  Val  Leu  Gly  Asn  Leu  Asn
     1310                1315                1320

Ser  Leu  Ala  His  Glu  Ala  Ile  Met  Cys  Ser  Tyr  Asn  Lys  Asp  Val
     1325                1330                1335

Pro  Val  Thr  Asp  Val  Leu  Tyr  Pro  Phe  Gly  Cys  Tyr  Asn  Ile  Ala
     1340                1345                1350

Pro  Ala  Val  Asp  Trp  Ile  Arg  Arg  Tyr  Thr  Leu  Ser  Ile  Phe  Ile
     1355                1360                1365

Val  Phe  Phe  Ile  Ser  Phe  Ile  Pro  Leu  Val  Val  Gln  Glu  Leu  Ile
     1370                1375                1380

Glu  Arg  Gly  Val  Trp  Lys  Ala  Phe  Gln  Arg  Phe  Val  Arg  His  Phe
     1385                1390                1395

Ile  Ser  Met  Ser  Pro  Phe  Phe  Glu  Val  Phe  Val  Ala  Gln  Ile  Tyr
     1400                1405                1410

Ser  Ser  Ser  Val  Phe  Thr  Asp  Leu  Thr  Val  Gly  Gly  Ala  Arg  Tyr
     1415                1420                1425
```

```
Ile Ser Thr Gly Arg Gly Phe Ala Thr Ser Arg Ile Pro Phe Ser
1430                1435                1440

Ile Leu Tyr Ser Arg Phe Ala Asp Ser Ser Ile Tyr Met Gly Ala
1445                1450                1455

Arg Leu Met Leu Ile Leu Leu Phe Gly Thr Val Ser His Trp Gln
1460                1465                1470

Ala Pro Leu Leu Trp Phe Trp Ala Ser Leu Ser Ala Leu Met Phe
1475                1480                1485

Ser Pro Phe Ile Phe Asn Pro His Gln Phe Ala Trp Glu Asp Phe
1490                1495                1500

Phe Leu Asp Tyr Arg Asp Phe Ile Arg Trp Leu Ser Arg Gly Asn
1505                1510                1515

Thr Lys Trp His Arg Asn Ser Trp Ile Gly Tyr Val Arg Leu Ser
1520                1525                1530

Arg Ser Arg Ile Thr Gly Phe Lys Arg Lys Leu Thr Gly Asp Val
1535                1540                1545

Ser Glu Lys Ala Ala Gly Asp Ala Ser Arg Ala His Arg Ser Asn
1550                1555                1560

Val Leu Phe Ala Asp Phe Leu Pro Thr Leu Ile Tyr Thr Ala Gly
1565                1570                1575

Leu Tyr Val Ala Tyr Thr Phe Ile Asn Ala Gln Thr Gly Val Thr
1580                1585                1590

Ser Tyr Pro Tyr Glu Ile Asn Gly Ser Thr Asp Pro Gln Pro Val
1595                1600                1605

Asn Ser Thr Leu Arg Leu Ile Ile Cys Ala Leu Ala Pro Val Val
1610                1615                1620

Ile Asp Met Gly Cys Leu Gly Val Cys Leu Ala Met Ala Cys Cys
1625                1630                1635

Ala Gly Pro Met Leu Gly Leu Cys Cys Lys Lys Thr Gly Ala Val
1640                1645                1650

Ile Ala Gly Val Ala His Gly Val Ala Val Ile Val His Ile Ile
1655                1660                1665

Phe Phe Ile Val Met Trp Val Thr Glu Gly Phe Asn Phe Ala Arg
1670                1675                1680

Leu Met Leu Gly Ile Ala Thr Met Ile Tyr Val Gln Arg Leu Leu
1685                1690                1695

Phe Lys Phe Leu Thr Leu Cys Phe Leu Thr Arg Glu Phe Lys Asn
1700                1705                1710

Asp Lys Ala Asn Thr Ala Phe Trp Thr Gly Lys Trp Tyr Asn Thr
1715                1720                1725

Gly Met Gly Trp Met Ala Phe Thr Gln Pro Ser Arg Glu Phe Val
1730                1735                1740

Ala Lys Ile Ile Glu Met Ser Glu Phe Ala Gly Asp Phe Val Leu
1745                1750                1755

Ala His Ile Ile Leu Phe Cys Gln Leu Pro Leu Leu Phe Ile Pro
1760                1765                1770

Leu Val Asp Arg Trp His Ser Met Met Leu Phe Trp Leu Lys Pro
1775                1780                1785

Ser Arg Leu Ile Arg Pro Pro Ile Tyr Ser Leu Lys Gln Ala Arg
1790                1795                1800

Leu Arg Lys Arg Met Val Arg Lys Tyr Cys Val Leu Tyr Phe Ala
1805                1810                1815

Val Leu Ile Leu Phe Ile Val Ile Ile Val Ala Pro Ala Val Ala
1820                1825                1830
```

```
Ser Gly Gln Ile Ala Val Asp Gln Phe Ala Asn Ile Gly Gly Ser
    1835                1840                1845

Gly Ser Ile Ala Asp Gly Leu Phe Gln Pro Arg Asn Val Ser Asn
    1850                1855                1860

Asn Asp Thr Gly Asn His Arg Pro Lys Thr Tyr Thr Trp Ser Tyr
    1865                1870                1875

Leu Ser Thr Arg Phe Thr Gly Ser Thr Thr Pro Tyr Ser Thr Asn
    1880                1885                1890

Pro Phe Arg Val
    1895

<210> SEQ ID NO 3
<211> LENGTH: 8
<212> TYPE: PRT
<213> ORGANISM: Artificial Sequence
<220> FEATURE:
<223> OTHER INFORMATION: amino acids 639-646 from S. cerevisiae Fks1p

<400> SEQUENCE: 3

Phe Leu Val Leu Ser Leu Arg Asp
1               5

<210> SEQ ID NO 4
<211> LENGTH: 8
<212> TYPE: PRT
<213> ORGANISM: Artificial Sequence
<220> FEATURE:
<223> OTHER INFORMATION: amino acids 641-648 of C. albicans Fks1p

<400> SEQUENCE: 4

Phe Leu Thr Leu Ser Leu Arg Asp
1               5

<210> SEQ ID NO 5
<211> LENGTH: 20
<212> TYPE: DNA
<213> ORGANISM: Artificial Sequence
<220> FEATURE:
<223> OTHER INFORMATION: sequencing primer

<400> SEQUENCE: 5
cattgctgtg gccactttag                                              20

<210> SEQ ID NO 6
<211> LENGTH: 21
<212> TYPE: DNA
<213> ORGANISM: Artificial Sequence
<220> FEATURE:
<223> OTHER INFORMATION: sequencing primer

<400> SEQUENCE: 6
gatttccatt tccgtggtag c                                            21

<210> SEQ ID NO 7
<211> LENGTH: 20
<212> TYPE: DNA
<213> ORGANISM: Artificial Sequence
<220> FEATURE:
<223> OTHER INFORMATION: PCR primer

<400> SEQUENCE: 7
gccaaattgg ttgaatctta                                              20

<210> SEQ ID NO 8
```

```
<211> LENGTH: 20
<212> TYPE: DNA
<213> ORGANISM: Artificial Sequence
<220> FEATURE:
<223> OTHER INFORMATION: PCR primer

<400> SEQUENCE: 8
gtcatggtcg acaagtttct                                                 20

<210> SEQ ID NO 9
<211> LENGTH: 32
<212> TYPE: DNA
<213> ORGANISM: Artificial Sequence
<220> FEATURE:
<223> OTHER INFORMATION: wild type target

<400> SEQUENCE: 9
aaaaatctct taaagacaaa gtcaagaaaa aa                                    32

<210> SEQ ID NO 10
<211> LENGTH: 31
<212> TYPE: DNA
<213> ORGANISM: Artificial Sequence
<220> FEATURE:
<223> OTHER INFORMATION: mutation target

<400> SEQUENCE: 10
aaaaatctct taaaggcaaa gtcaagaaaa a                                     31

<210> SEQ ID NO 11
<211> LENGTH: 33
<212> TYPE: DNA
<213> ORGANISM: Artificial Sequence
<220> FEATURE:
<223> OTHER INFORMATION: mutation target

<400> SEQUENCE: 11
aaaaatctct taaatacaaa gtcaagaaga aaa                                   33

<210> SEQ ID NO 12
<211> LENGTH: 33
<212> TYPE: DNA
<213> ORGANISM: Artificial Sequence
<220> FEATURE:
<223> OTHER INFORMATION: mutation target

<400> SEQUENCE: 12
aaaaatctct taaaacaaa gtcaagaaga aaa                                    33

<210> SEQ ID NO 13
<211> LENGTH: 32
<212> TYPE: DNA
<213> ORGANISM: Artificial Sequence
<220> FEATURE:
<223> OTHER INFORMATION: SNP target

<400> SEQUENCE: 13
aaaaatctct taaagacaat gtcaagaaaa aa                                    32

<210> SEQ ID NO 14
<211> LENGTH: 31
<212> TYPE: DNA
<213> ORGANISM: Artificial Sequence
<220> FEATURE:
<223> OTHER INFORMATION: mutation target

<400> SEQUENCE: 14
```
aaaaatctct taaaggcaat gtcaagaaaa a                           31

<210> SEQ ID NO 15
<211> LENGTH: 33
<212> TYPE: DNA
<213> ORGANISM: Artificial Sequence
<220> FEATURE:
<223> OTHER INFORMATION: mutation target

<400> SEQUENCE: 15
aaaaatctct taaatacaat gtcaagaaga aaa                         33

<210> SEQ ID NO 16
<211> LENGTH: 33
<212> TYPE: DNA
<213> ORGANISM: Artificial Sequence
<220> FEATURE:
<223> OTHER INFORMATION: mutation target

<400> SEQUENCE: 16
aaaaatctct taaaaacaat gtcaagaaga aaa                         33

<210> SEQ ID NO 17
<211> LENGTH: 36
<212> TYPE: DNA
<213> ORGANISM: Artificial Sequence
<220> FEATURE:
<223> OTHER INFORMATION: wild type probe

<400> SEQUENCE: 17
cgcgagttct tgacwttgtc tttaagagat ctcgcg                      36

<210> SEQ ID NO 18
<211> LENGTH: 35
<212> TYPE: DNA
<213> ORGANISM: Artificial Sequence
<220> FEATURE:
<223> OTHER INFORMATION: mutation probe

<400> SEQUENCE: 18
cgcgagtctt gacwttgcct ttaagagatc tcgcg                       35

<210> SEQ ID NO 19
<211> LENGTH: 37
<212> TYPE: DNA
<213> ORGANISM: Artificial Sequence
<220> FEATURE:
<223> OTHER INFORMATION: mutation probe

<400> SEQUENCE: 19
cgcgagcttc ttgacwttgt atttaagaga tctcgcg                     37

<210> SEQ ID NO 20
<211> LENGTH: 37
<212> TYPE: DNA
<213> ORGANISM: Artificial Sequence
<220> FEATURE:
<223> OTHER INFORMATION: mutation probe

<400> SEQUENCE: 20
cgcgagcttc ttgacwttgt ttttaagaga tctcgcg                     37

<210> SEQ ID NO 21
<211> LENGTH: 21
<212> TYPE: DNA
<213> ORGANISM: Artificial Sequence
<220> FEATURE:

<223> OTHER INFORMATION: PCR primer

<400> SEQUENCE: 21
gaaatcggca tatgctgtgt c                                              21

<210> SEQ ID NO 22
<211> LENGTH: 21
<212> TYPE: DNA
<213> ORGANISM: Artificial Sequence
<220> FEATURE:
<223> OTHER INFORMATION: PCR primer

<400> SEQUENCE: 22
aatgaacgac caatggagaa g                                              21

<210> SEQ ID NO 23
<211> LENGTH: 20
<212> TYPE: DNA
<213> ORGANISM: Artificial Sequence
<220> FEATURE:
<223> OTHER INFORMATION: sequencing primer

<400> SEQUENCE: 23
cattgctgtg gccactttag                                                20

<210> SEQ ID NO 24
<211> LENGTH: 20
<212> TYPE: DNA
<213> ORGANISM: Artificial Sequence
<220> FEATURE:
<223> OTHER INFORMATION: sequencing primer

<400> SEQUENCE: 24
ggtcaaatca gtgaaaaccg                                                20

<210> SEQ ID NO 25
<211> LENGTH: 23
<212> TYPE: DNA
<213> ORGANISM: Artificial Sequence
<220> FEATURE:
<223> OTHER INFORMATION: PCR primer

<400> SEQUENCE: 25
ccatttggtt gttacaatat tgc                                            23

<210> SEQ ID NO 26
<211> LENGTH: 23
<212> TYPE: DNA
<213> ORGANISM: Artificial Sequence
<220> FEATURE:
<223> OTHER INFORMATION: PCR primer

<400> SEQUENCE: 26
ccaatggaat gaaagaaatg aag                                            23

<210> SEQ ID NO 27
<211> LENGTH: 36
<212> TYPE: DNA
<213> ORGANISM: Artificial Sequence
<220> FEATURE:
<223> OTHER INFORMATION: wild type probe

<400> SEQUENCE: 27
cgcgaggatt ggattagacg ttatactttg ctcgcg                              36

<210> SEQ ID NO 28

```
<211> LENGTH: 36
<212> TYPE: DNA
<213> ORGANISM: Artificial Sequence
<220> FEATURE:
<223> OTHER INFORMATION: mutant probe

<400> SEQUENCE: 28
cgcgaggatt ggattagaca ttatactttg ctcgcg                              36
```